(12) United States Patent
Bullington et al.

(10) Patent No.: US 7,675,674 B2
(45) Date of Patent: Mar. 9, 2010

(54) HIGH-POWER-OPTICAL-AMPLIFIER USING A NUMBER OF SPACED, THIN SLABS

(75) Inventors: Jeff Bullington, Chuluota, FL (US);
Richard Stoltz, Plano, TX (US);
Michael Mielke, Orlando, FL (US)

(73) Assignee: Raydiance, Inc., Petaluma, CA (US)

( * ) Notice: Subject to any disclaimer, the term of this patent is extended or adjusted under 35 U.S.C. 154(b) by 561 days.

(21) Appl. No.: 10/568,135

(22) PCT Filed: Aug. 11, 2004

(86) PCT No.: PCT/US2004/025989

§ 371 (c)(1),
(2), (4) Date: Oct. 19, 2006

(87) PCT Pub. No.: WO2005/018060

PCT Pub. Date: Feb. 24, 2005

(65) Prior Publication Data

US 2007/0041082 A1 Feb. 22, 2007

Related U.S. Application Data

(60) Provisional application No. 60/494,102, filed on Aug. 11, 2003, provisional application No. 60/494,272, filed on Aug. 11, 2003, provisional application No. 60/494,321, filed on Aug. 11, 2003, provisional application No. 60/497,404, filed on Aug. 22, 2003, provisional application No. 60/503,659, filed on Sep. 17, 2003, provisional application No. 60/503,578, filed on Sep. 17, 2003, provisional application No. 60/529,425, filed on Dec. 12, 2003, provisional application No. 60/529,443, filed on Dec. 11, 2003, provisional application No. 60/543,086, filed on Feb. 9, 2004, provisional application No. 60/546,065, filed on Feb. 18, 2004, provisional application No. 60/548,216, filed on Feb. 26, 2004.

(51) Int. Cl.
*H01S 3/00* (2006.01)

(52) U.S. Cl. ........................................ 359/333; 372/35

(58) Field of Classification Search .................. 372/35, 372/33; 359/333
See application file for complete search history.

(56) References Cited

U.S. PATENT DOCUMENTS

| 3,602,836 | A | * | 8/1971 | Young | 372/67 |
| 3,628,179 | A | * | 12/1971 | Cuff | 372/35 |
| 3,696,308 | A | * | 10/1972 | Duffy et al. | 372/67 |
| 3,735,282 | A | * | 5/1973 | Gans | 372/67 |
| 6,937,629 | B2 | * | 8/2005 | Perry et al. | 372/35 |
| 2003/0161365 | A1 | * | 8/2003 | Perry et al. | 372/35 |

* cited by examiner

*Primary Examiner*—Mark Hellner
(74) *Attorney, Agent, or Firm*—Carr & Ferrell LLP

(57) ABSTRACT

The high-power-optical-amplifier of the present invention uses a number of spaced, thin slabs (e.g., disc-shaped doped-slabs that are stacked, with a space between discs), aligned to give an amplifier both with a high active cross-section and a very high surface area to volume ratio. More specifically, the present invention provides several methods that include the steps of aligning at least two or four slabs having a thickness dimension of less than one centimeter, substantially parallel to, and spaced from adjacent slabs, wherein the slab surfaces are rendered essentially non-reflective, optically pumping the slabs and passing an input beam through the surfaces wherein the beam is optically amplified in the slabs, and wherein the input beam is of an eye-safe wavelength.

18 Claims, 12 Drawing Sheets

HIGH-POWER-OPTICAL-AMPLIFIER USING A NUMBER OF SPACED, THIN SLABS

This patent application claims priority to the following previously filed United States provisional patent applications:

| Docket. Number | Title | U.S. Ser. No. | Filing Date |
| --- | --- | --- | --- |
| ABI-8 | Controlling Repetition Rate Of Fiber Amplifier | 60/494,102 | Aug. 11, 2003 |
| ABI-12 | Fiber Amplifier With A Time Between Pulses Of A Fraction Of The Storage Lifetime | 60/494,272 | Aug. 11, 2003 |
| ABI-13 | Man-Portable Optical Ablation System | 60/494,321 | Aug. 11, 2003 |
| ABI-19 | High-Power-Optical-Amplifier Using a Number of Spaced, Thin Slabs | 60/497,404 | Aug. 22, 2003 |
| ABI-22 | Active Optical Compressor | 60/503,659 | Sep. 17, 2003 |
| ABI-23 | Controlling Optically-Pumped Optical Pulse Amplifiers | 60/503,578 | Sep. 17, 2003 |
| ABI-28 | Quasi-Continuous Current in Optical Pulse Amplifier Systems | 60/529,425 | Dec. 12, 2003 |
| ABI-29 | Optical Pulse Stretching and Compression | 60/529,443 | Dec. 11, 2003 |
| ABI-33 | Semiconductor-Type Processing for Solid-State Lasers | 60/543,086 | Feb. 09, 2004 |
| ABI-34 | Pulse Streaming of Optically-Pumped Amplifiers | 60/546,065 | Feb. 18, 2004 |
| ABI-35 | Pumping of Optically-Pumped Amplifiers | 60/548,216 | Feb. 26, 2004 |

TECHNICAL FIELD

The present invention relates in general to the field of light amplification and, more particularly, to high-power-optical-amplifier using a number of spaced, thin slabs.

BACKGROUND ART

Ablative material removal is especially useful for medical purposes, either in-vivo or on the outside surface (e.g., skin or tooth), as it is essentially non-thermal and generally painless. Moreover, ablative material removal essentially exerts no pressure on the surface of the material, so it is quite useful for many other types of cutting and machining. Ablative material removal is generally done with a short optical pulse that is stretched amplified and then compressed. A number of types of laser amplifiers have been used for the amplification, including fiber amplifiers. Fiber amplifiers have a storage lifetime of about 100 to 300 microseconds. While some measurements have been made at higher repetition rates, these measurements have shown an approximately linear decrease in pulse energy. For ablations purposes, fiber amplifiers have been operated with a time between pulses of equal to or greater than the storage lifetime, and thus are generally run a repetition rate of less than 3-10 kHz.

Laser ablation is very efficiently done with a beam of very short pulses (generally a pulse-duration of three picoseconds or less). While some laser machining melts portions of the work-piece, this type of material removal is ablative, disassociating the surface atoms. Techniques for generating these ultra-short pulses are described, e.g., in a book entitled "Femtosecond Laser Pulses" (C. Rulliere—editor), published 1998, Springer-Verlag Berlin Heidelberg New York. Generally large systems, such as Ti:Sapphire, are used for generating ultra-short pulses (USP). When high-power pulses are desired, they are often intentionally lengthened before amplification to avoid thermally-induced internal component optical damage. Techniques for surface gratings are described in "Zero Reflectivity High Spatial Frequency Rectangular Groove Dielectric Surface Relief Gratings" by Thomas Gaylord, et. al. Dec. 15, 1986, Applied Optics, Vol. 25, pp. 4562-4567.

USP phenomenon was first observed in the 1970's, when it was discovered that mode-locking a broad-spectrum laser could produce ultra-short pulses. The minimum pulse duration attainable is limited by the bandwidth of the gain medium, which is inversely proportional to this minimal or Fourier-transform-limited pulse duration. Mode-locked pulses are typically very short and will spread (i.e., undergo temporal dispersion) as they traverse any medium. Subsequent pulse-compression techniques are often used to obtain USP's. A traditional diffraction grating compressor is shown, e.g., in U.S. Pat. No. 5,822,097 by Tournois. Pulse dispersion can occur within the laser cavity so that compression techniques are sometimes added intra-cavity. Previous approaches have generally operated maximum-sized amplifiers at maximum power and amplified longer and longer pulses. When high-power pulses are desired, they are intentionally lengthened before amplification to avoid internal component optical damage. This is referred to as "Chirped Pulse Amplification" (CPA). The pulse is subsequently compressed to obtain a high peak power (pulse-energy amplification and pulse-duration compression).

SUMMARY OF THE INVENTION

The high-power-optical-amplifier of the present invention uses a number of spaced, thin slabs (e.g., disc-shaped doped-glass-slabs that are stacked, with a space between discs), aligned to give an amplifier both with a high active cross-section and a very high surface area to volume ratio. The low-absorption, eye-safe (e.g., 1400 to 1800 nm) laser beam being amplified is passed through the thin dimension of the slabs. Cooling fluid (e.g., gas) can pass between the slabs and provide exceptionally good heat transfer because of the high surface area, and the very short distance the heat has to travel to reach the surface of the thin slabs. The slabs are generally optically pumped at an angle to the direction of beam travel (e.g., in a radial direction).

The beam travels through the thin dimension of slabs and passes through surfaces that have very low reflectivity, with the surface reflectivity being reduced at least one of (and preferably both of) surfaces being placed near the Brewster angle with respect to the polarized beam, and A/R surface coatings. Within the slab, opposing slab surfaces are generally approximately, but not precisely parallel, to further reduce internal slab reflections. In addition, lasing due to reflections within the amplifier are generally even further reduced by avoiding any slab surfaces within the amplifier being precisely parallel.

Thus eye-safe laser beam being amplified is passed through the thin dimension of the slabs and the beam travels efficiently through surfaces that have extremely low reflectivity and the use of nonparallel surfaces throughout the amplifier further increases efficiency by avoiding lasing of reflected light. Still further, the method generally uses sub-ten-picosecond pulses for highly-efficient ablative machining, even further increasing efficiency. Controlling reflections and use of multiple relatively thin slabs to reduce slab temperature greatly increases efficiency. The high efficiency and an eye-safe beam wavelength makes the system practical for use (e.g., commercial) outside of research laboratories.

Preferably, the slabs are directly diode pumped and are not greater than 3 mm in thickness (and other dimensions preferably are of at least 5 mm). Further, half the slabs are preferably slanted in one direction and the other half are slanted in the opposite direction to avoid beam spreading.

In many embodiments, A/R coatings are placed on the slabs to make the structure less polarization specific (Brewster angles for reducing reflections are polarization specific), for increased optical pumping efficiency. The A/R coatings may either be multi-layer or single layer dielectric coatings. The A/R structure's design may be two dimensional to have low reflectivity in both polarization axes of the incident radiation.

A Brewster angle arrangement with all slabs tilted (slanted) in the same direction does give some spatial spreading due to small wavelength variations (e.g., changing a ray into a line, or a line to an area). Slanting half the slabs in on direction and half in the other direction compensates and avoids beam spreading in the output beam. A prism can also change the line back into a ray. A mirror can alternately be used to reflect the beam back through slabs all tilted in the one direction to compensate for beam spreading.

In some embodiments, there can be some advantage to have spatial spreading during amplification, as it increases the effective cross-sectional area of the amplifier. For example, a dot-shaped beam can be entered into the amplifier, and spread into a larger area (e.g., an ellipse) during amplification (with all slabs tilted in the same direction), the area of the output beam can then be optically reduced, e.g., with reflective optics. Generally, however, the use of slanting half the slabs in on direction and half in the other direction, is preferred.

The Brewster angle arrangement also can give some time spreading (or, if the pulse is stretched in the opposite manner, compressing) due to the fact that different wavelengths can have different path lengths through the slabs. In our preferred chirp pulse amplification, the pulse is stretched and compressed, and the time-spreading can be compensated for during either the stretching or compressing. If the slabs are all tilted in the same direction and the pulse is stretched in the right manner, this can replace at least part of the compression.

The present invention provides a method of amplifying an optical beam with a number of spaced, optical-amplifier slabs, with the slabs having two surfaces perpendicular to a thickness dimension, comprising: aligning at least four slabs having a thickness dimension of less than one centimeter (preferably less than 2 millimeters) with surfaces parallel to, and spaced from adjacent slabs, wherein the slabs surfaces are rendered essentially non-reflective by being placed at the Brewster angle with respect to optical input beam, optically pumping the slabs, and passing a polarized input beam through the surfaces wherein the beam is optically amplified in the slabs, and wherein the input beam is of an eye-safe wavelength.

Preferably, truly parallel surfaces are avoided by slightly changing angles (e.g., by 0.1 to 1 degree). This avoids the internal lasing from back-reflections between parallel surfaces (as practical A/R coatings are less than perfect, and there is some beam bandwidth and Brewster angle surfaces thus also have a small reflection).

In addition, the present invention provides a method of amplifying an optical beam with a number of spaced, optical-amplifier slabs, with the slabs having two surfaces within 1 degree of perpendicular to a thickness dimension (e.g., wedge-shaped) by aligning at least four slabs having a thickness dimension of less than one centimeter (preferably less than 2 millimeters) with surfaces within 1 degree of parallel to, and spaced from adjacent slabs, wherein the slabs surfaces are rendered essentially non-reflective by being placed at the Brewster angle with respect to optical input beam; optically pumping the slabs, and passing a polarized input beam through the surfaces wherein the beam is optically amplified in the slabs, and wherein the input beam is of an eye-safe wavelength. Thus, the slab surfaces are very close to parallel (e.g., less than 1 degree from parallel), but the internal lasing that would be caused by amplification between two parallel reflectors (even surfaces of very low reflectivity) is avoided.

Preferably the at least four slabs are placed at about a Brewster angle to the beam and tilting in one direction and the beam also passes through a same number of opposite-tilting slabs, wherein using slabs slanting in an opposite direction avoids beam spreading in the output beam. In addition, the slabs are preferably pumped directly by pump diodes (some prior art systems have used diodes to pump pump-lasers or used lamp-pumping). Preferably, the slabs are Cr:YAG slabs. The beam preferably has a wavelength of between 1500 and 1600 nm. Moreover, cooling fluid can be passed between the slabs.

In some embodiments, the slabs surfaces are rendered essentially non-reflective both by surface gratings and by being placed at the Brewster angle with respect to a polarized optical input beam. The slabs may be placed at a Brewster angle with all slabs tilted in the same direction and a line-shaped beam is entered into the amplifier, and spread into an area during amplification, and the area of the output beam then optically reduced.

The present invention also provides a method of amplifying an optical beam with a number of spaced, optical-amplifier-slabs, with the slabs having two surfaces perpendicular to a thickness dimension by aligning at least two slabs having a thickness dimension of less than one centimeter, with surfaces parallel to, and spaced from adjacent slabs, and with slabs surfaces being rendered essentially non-reflective by being placed at the Brewster angle with respect to a polarized optical input beam, optically pumping the slabs, and passing the polarized input beam of eye-safe wavelength through the surfaces wherein the beam is optically amplified in the slabs.

Moreover, the present invention provides a method of amplifying an optical beam with a number of spaced, doped-slabs, with the slabs having two surfaces perpendicular to a thickness dimension (generally the smallest dimension of the slab) by aligning at least five of slabs having a thickness dimension of less than one centimeter with surfaces parallel to, and spaced from adjacent slabs, and with slabs surfaces being rendered essentially non-reflective by either surface gratings or being placed at the Brewster angle with respect to a polarized optical input beam; optically pumping the slabs, and passing the polarized input beam through the surfaces and the beam is optically amplified in the slabs. Preferably the thickness dimension is less than 2 millimeters. Preferably at least ten, and more preferably at least 16, aligned slabs are used in one amplifier.

BRIEF DESCRIPTION OF THE DRAWINGS

Other characteristics of the invention may be better understood using the following drawings, in which.

DESCRIPTION OF THE INVENTION

Figure 1:
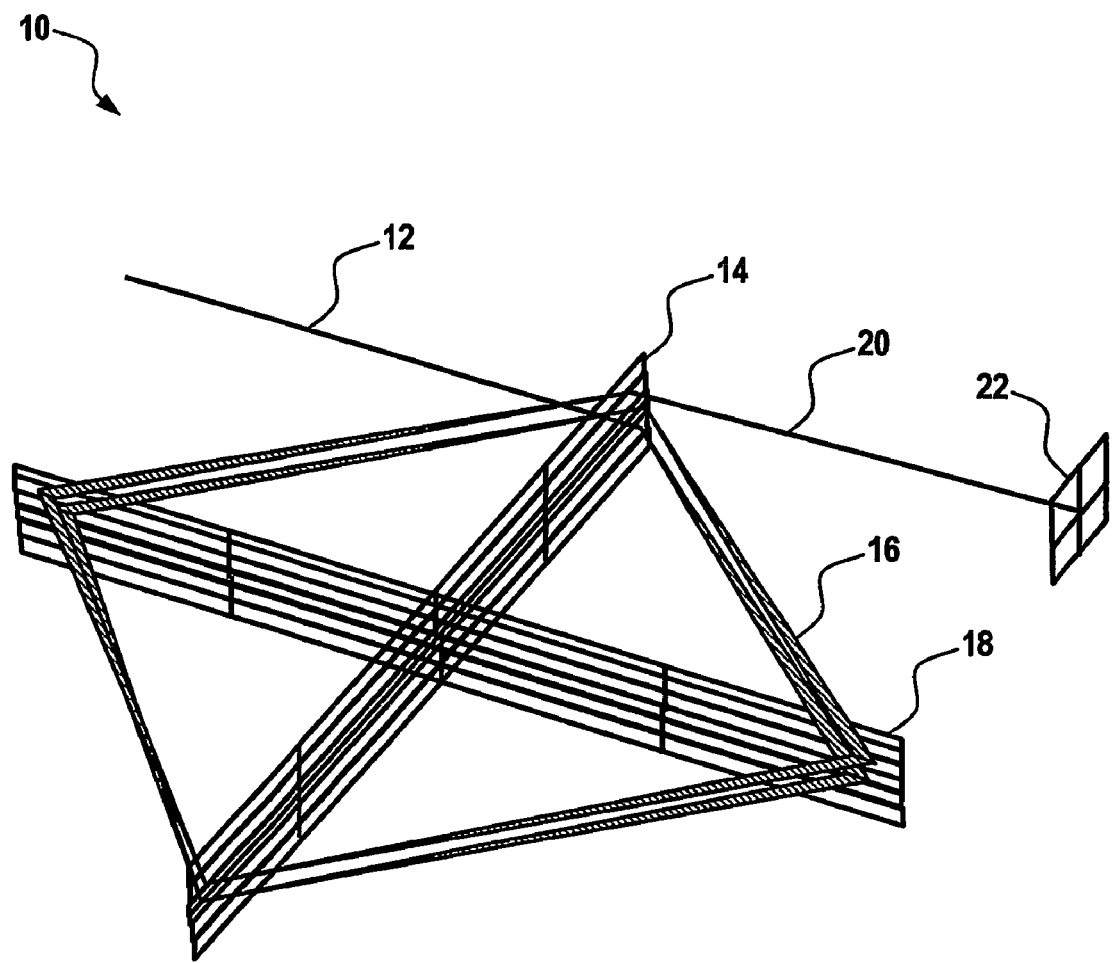
FIG. 1 is an isometric of transmissive gratings that stretch or compress a pulse and shows a beam traveling in a generally helical path.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Laser machining is most efficiently done with a beam of very short pulses (generally a pulse-duration of three picoseconds or less) in a controlled range of energy density (generally about 0.1 to 20 Joules/square centimeter, and preferably 0.1 to 8 Joules/square centimeter). While lasers can remove a slit of material, e.g., 500 microns wide, it has been found that most cutting tasks on most materials (including metals), can be much more efficiently done as a line of small diameter perforations (e.g., 25 micron holes on 40 micron centers), which allows the material to break cleanly along the line with little or no application of additional force. Thus, the amount of material that needs to be removed is greatly reduced and the small spot size reduces the required power and allows machining with smaller and less expensive lasers (including portable semiconductor-chip-diode systems). Perforation machining with tapered holes is also much more practical as channeling of the energy within a hole generally causes the hole diameter to taper down with depth (while the hole diameter can be made relatively constant, this is generally unnecessary and consumes more energy).

It has also been found that with the controlled energy density, however, that in many instances, holes formed by a single pulse (and often even several pulses) do not sufficiently penetrate the work-piece to give a clean break. Further, due to the small diameter of the laser beam, relative motion (e.g., vibration) between the laser beam and the work-piece can prevent successive pulses from hitting the same hole, thus preventing sufficient penetration. Even in other laser machining, e.g., when the surface is being ablated, rather than a hole produced, movement such as vibration can cause uneven ablation. Note that other uses such as surgical procedures can use surface ablation or cutting, and can use overlapping ablation to produce a cut surface, rather than a series of holes. In all such uses, a train of pulses is preferably generated by one or more semiconductor-chip diodes. Note also, the train of pulses allows a quasi-continuous wave operation that improves system efficiency, e.g., lessening the number of power up-ramps and down-ramps.

Typically a line of laser-produced holes (including a circle of small holes to create a large hole) is desired. There are, however, applications where a single laser-produced hole completely penetrating a work-piece is desired. Again, vibration or other motion can interfere with efficient production of such a hole.

It has also been found that the smaller and less expensive lasers (e.g., semiconductor-chip diodes) can generate a train of femtosecond pulses at intervals of a few nanoseconds for up to a few microseconds without overheating. As there are generally only a few nanoseconds between the pulses, and as channeling guides energy down the hole even if the beam and hole centerlines are offset by a few microns, relative motion would have to be many times supersonic to prevent multiple pulses from entering each laser-produced hole.

One embodiment of the present invention provides a method of perforation laser-machining that includes generating at least one 0.01 to 10 microsecond-long train of pulses, each pulse having a pulse-duration of 50 femtoseconds to three picoseconds, with the pulses being at intervals of 1 to 20 nanoseconds, and directing a beam of the pulses to a work-piece with a pulse-energy-density of 0.1 to 20 Joules/square centimeter to produce one or more holes in the work-piece. The holes may be, e.g., 10 to 150 micron holes on centers 15 to 300 microns. Preferably, the train of pulses are 0.05 to 1 microsecond-long, the pulse-duration is 50 femtoseconds to 1 picoseconds, pulses at intervals are 1 to 10 nanoseconds, and the pulse-energy-density is between 1 and 8 Joules/square centimeter on the work-piece. The holes are preferably 20 to 100 micron holes on centers 15 to 200 microns.

For example, a 100 femtosecond pulse can be time-stretched to make an optical pulse signal ramp (of, e.g., increasing, wavelength) which is amplified (at comparatively low instantaneous power), and time-compressed into an amplified 100 femtosecond pulse. Generally a series of pulses are generated, and thus a series of wavelength-ramps are used (e.g., a "saw-tooth" waveform with 50 "teeth" may be amplified by the SOAs without turning the current off between the teeth). Thus although the amplifiers are amplifying continuously during the 50-tooth waveform, the time-compression will separate the optical output into 50 separate pulses.

Semiconductor laser diodes are highly preferred for generating the ultra-short pulses. Semiconductor laser diodes typically are of III-V compounds (composed of one or more elements from the third column of the periodic table and one or more elements from the fifth column of the periodic table, e.g., GsAs, AlGaAs, InP, InGaAs, or InGaAsP). Other materials, such as II-VI compounds, e.g., ZnSe, can also be used. Typically lasers are made up of layers of different III-V compounds (generally, the core layer has higher index of refraction than the cladding layers to generally confine the light to a core). Semiconductor lasers have been described (see Rulliere, Chapter 5). It should be noted that this method works especially with semiconductor-chip diodes. Semiconductor-chip diodes can have high efficiency (e.g., about 50%) and have short energy-storage-lifetimes (e.g., a few nanoseconds). With a small, e.g., 20 micron spot, the ablating energy can be furnished by a single semiconductor optical amplifier (SOA) putting out less than 10 micro-Joules per pulse (which low energy density also limits collateral damage). The other types of lasers (e.g., Ti:sapphire) generally have energy-storage-lifetimes (e.g., in the hundreds of microsecond range), and this is convenient for accumulating energy and releasing it in a short period of time as a high-energy pulse. These other type of lasers have generally been used for generating short, high energy pulses, but their efficiencies are low (generally less than 1%) and the pulse energies drop off rapidly when operated at high repetition rates (when they begin to heat up, and when time between pulses becomes short and starts to reduce the time for accumulating energy for the next pulse). Conversely, semiconductor-chip diodes can provide a microsecond long train of pulses of nearly constant energy with nanosecond spacings. Thus while other types of lasers could be used, semiconductor-chip diodes are preferred.

The examples used herein are to be viewed as illustrations rather than restrictions, and the invention is intended to be limited only by the claims. For example, the invention applies not only to GaAs and InP (which generates light within it III-V semiconductor structure at a wavelength of about 1550 nm) laser diodes, but also to other semiconductor materials such as II-VI compounds.

Ablation is most efficient at about three times the material's ablation threshold, and thus control of pulse energy density for optimum removal efficiency is very desirable. If the spot size is fixed or otherwise known, this can be achieved by controlling pulse energy; or if the pulse energy is known, by controlling spot size. The present invention uses a novel method of controlling the pulse energy by controlling the amplified pulse energy, which is much more convenient than changing the ablation spot size. It has been found that optically-pumped amplifiers are more effective operated at a fraction (e.g., less than about half) of their maximum stored energy. When operated in this manner, the pulse energy can be varied by controlling the repetition rate, as the amount of stored energy in the amplifier increases with the time between pulses.

It has been found that in fiber amplifiers, pulse energy control can be done step-wise by controlling repetition rate and can be fine-tuned by controlling optical pumping power.

The pulse energy of a semiconductor optical amplifier (SOA) can be adjusted by changing the current through the amplifier.

While the compressors in either type of system can be run with inputs from more than one amplifier, reflections from other of the parallel amplifiers can cause a loss of efficiency, and thus should be minimized (as used herein, "parallel" includes train mode). The loss is especially important if the amplifiers are amplifying signals at the same time, as is the case with the SOAs. Thus each off the parallel SOAs preferably has its own compressor and while the amplified pulses may be put into a single fiber after the compressors, reflections from the joining (e.g., in a star connector) are greatly reduced before getting back to the amplifier. With the fiber amplifiers, however, a nanosecond spacing of sub-nanosecond stretched pulses eliminates any amplifying of multiple signals at the same time, and a single compressor is preferably used.

The present invention uses one or more fiber amplifiers of moderate-power, with a short optical pulse that is amplified and then compressed into a very short pulse, and the light pulse focused onto a very small area spot. The system rapidly scans the spot over an area to be ablated and controls the pulse power to maximize ablation efficiency.

The present invention preferably uses parallel amplifiers (optically pumped or semiconductor optical amplifiers (SOAs)) to increase the ablation rate by further increasing the effective repetition rate (while avoiding thermal problems and allowing control of ablation rate by adjusting the number of operating amplifiers, and allowing control of ablation rate by the use of a lesser number of operating amplifiers). The use of more than one amplifier in parallel train mode (pulses from one amplifier being delayed to arrive one or more nanoseconds after, or a few picoseconds after, another amplifier) allows the ablation rate to be controlled largely independent of repetition rate.

The pump diodes and their power supply can be operated efficiently when operated with the electrical current is being supplied continuously (CW). In the past, ablation systems have been operated with laser materials with a long storage lifetime, e.g., one millisecond, and at low repetition rates, e.g., 1 KHz.

It has been found that an optically-pumped amplifier is more effectively operated at higher repetition rates such that the amplifiers reach only a fraction (e.g., less than about half) of their maximum stored energy, and that ablation is most effective at an energy density of about three times the ablation threshold for the material being ablated. The system of the present invention preferably uses a moderately short storage lifetime laser material (e.g., Cr:YAG with a few microsecond storage lifetime), with the amplifiers optically-pumped quasi-CW (e.g., pumping and amplifying in 1 millisecond long streams of pulses with 100 streams per second). During such streams, the pulse repetition rate may be, e.g., 1 MHz, and thus 1,000 pulses per stream.

The surface reflectivity is reduced either by the surfaces being placed near the Brewster angle with respect to the polarized beam and/or by use of surface A/R coatings (preferably both). Further, all slab surfaces within the amplifier are generally slightly non-parallel (including opposing surfaces of the slabs, as well as surfaces of other slabs) to increase efficiency. Still further, we also generally use ablative sub-ten-picosecond pulses.

The slabs may be optically pumped in a radial direction. The slabs may also be effectively pumped through their surfaces, especially when surface A/R coatings are used.

With quasi-CW, there is a pause between streams, which allows adjustment of the ratio of pause duration to stream duration, e.g., for amplifier temperature control. Operated in this manner, the pulse energy can be optimized by controlling the repetition rate within a range of increased amplifier efficiency, without over-heating system components.

During each stream (but not during the pause), continuous current is supplied to the diodes that supply the optically-pumped amplifier. As the pump diodes are turned off during the pauses, the temperature of the pump diodes can also be limited or otherwise controlled. In the optically-pumped amplifier, the input optical signal is a series pulses (each pulse, e.g., a 1 nanosecond long, wavelength-swept-with-time ramp). The pulses to the amplifier may be continued during the pause as amplification will stop due to lack of pumping, or SOAs used as preamplifiers may be turned off during the pauses to reduce temperature of the SOAs.

Thus, for example, with amplifiers directly pumped by pump diodes, optical pumped amplifiers can be effectively operated to amplify intermittent sub-millisecond streams (or bursts) of 1 MHz pulses (streams separated by pauses). The ratio of streaming time to pause time can be controlled to control amplifier temperature, and/or the ablation rate, and/or the temperature of the pump diodes). In the case where the system is to be operated at lower ablation rates, the ratio of streaming-time to pause-time can be controlled to vary the ablation rate.

Quasi-CW operation improves system efficiency. As the number of pulses per stream in CW can be large (there are comparatively few current up-ramps and down-ramps) and there is little lost in efficiency compared to CW, and there are significant increases in energy storage efficiency and the optimizing of pulse energy density.

Figure 4:
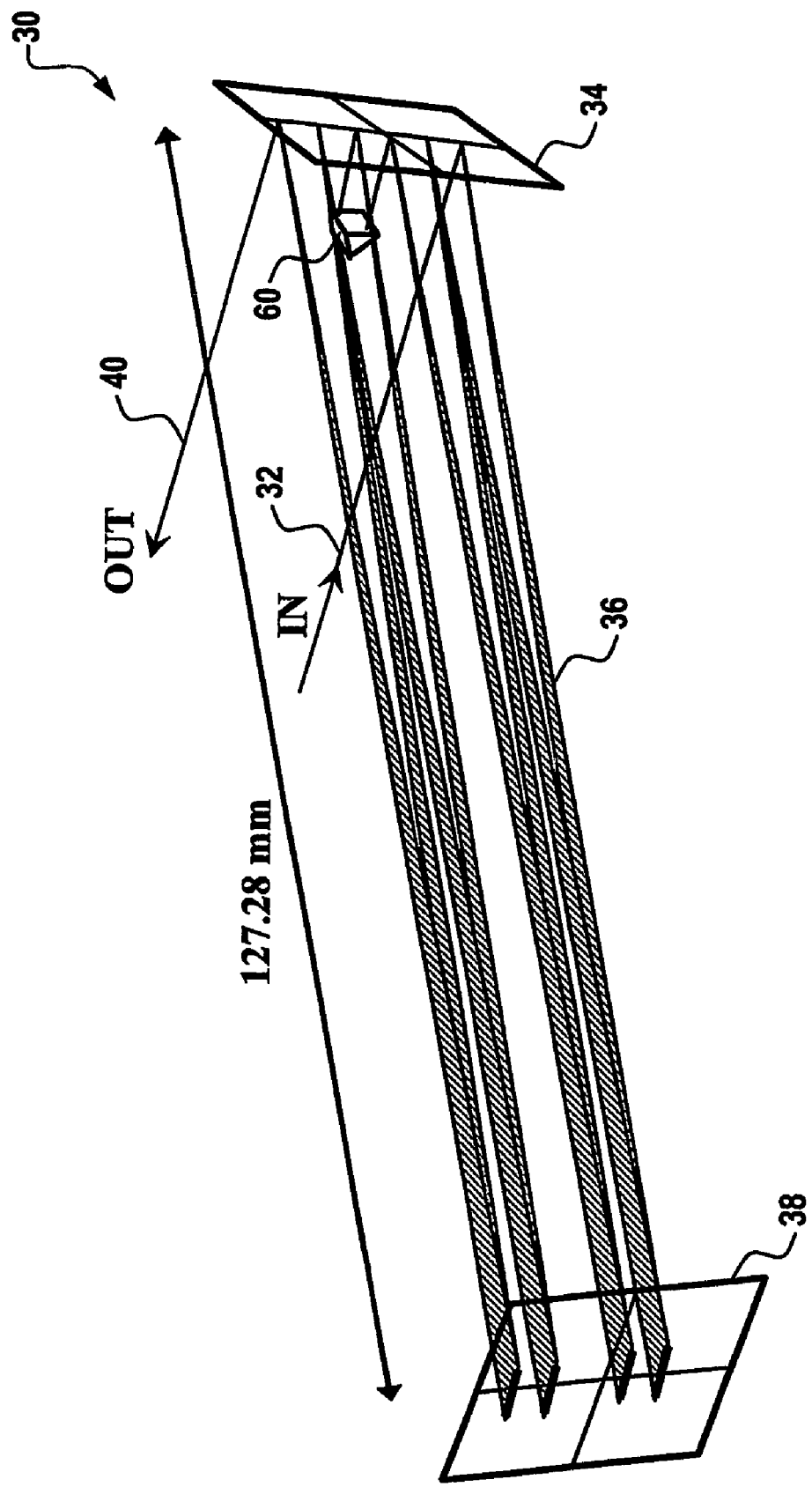
FIG. 4 shows an isometric of two reflective chirped gratings in Littrow Angle configuration and a retro-reflector for spatial-chirp correction.

Preferably, 1300 nm or above light is used for greater pulse compression efficiency that at shorter wavelengths. Specifically, 1550 mm light is used both for safety purposes, and for greater pulse compression efficiency. At 1550 nm compression is much more efficient than at shorter wavelengths. With longer distances between elements and/or more diffractions or reflections, higher stretching/compression factors can be obtained. The improved diffracting grating stretching/compressing method of the present invention uses inputting a tilted collimated beam, spatial-spreading the beam, spatial-narrowing the beam, spatial-spreading the beam, spatial-narrowing the beam, and collimating the beam output, wherein the beam hits at least one of the gratings more than once (because of the tilt, the beam hits such a grating at a different line or point each time around). The gratings may be transmissive and/or reflective (a device having transmissive gratings disposed at right angles, but with an un-tilted beam is shown in FIG. 4 of U.S. Pat. No. 5,822,097 by Tournois). In systems with larger tilts, e.g., more than ¾ degree, collimating an intermediate spatially-narrowed beam, then manipulating the beam to correct spatial-chirp, is necessary and can be done with, e.g., a retro-reflector mirror-pair or prism.

In such systems, the control of input optical signal power, optical pumping power of optically-pumped amplifiers, timing of input pulses, length of input pulses, and timing between start of optical pumping and start of optical signals to control pulse power, and average degree of energy storage in optically-pumped amplifier. While the examples herein have been largely for medical uses, the ablative material removal can be used for a wide variety of purposes, including virtually types of cutting operations (e.g., cutting high-tech composite materials).

In one embodiment, the present invention uses an optically-pumped-amplifier (e.g., a erbium-doped fiber amplifier or a Cr:YAG amplifier) and compressed by an air-path between gratings compressor (e.g., a Tracey grating compressor), with the compression creating a sub-picosecond ablation pulse. Generally a semiconductor oscillator is used to generate pulses and in some embodiments a SOA preamplifier is used to amplify the selected pulses before introduction into the optically-pumped amplifier.

Fiber amplifiers have a storage lifetime of about 100 to 300 microseconds. While measurements have been made at higher repetition rates, these measurements have shown an approximately linear decrease in pulse energy. For ablations purposes, power fiber amplifiers have generally been operated with a time between pulses about equal to than the storage lifetime (or at greater than the storage lifetime, to avoid thermal problems in the fiber), and thus are generally run a repetition rate of less than 3-10 kHz. Optically-pumped amplifiers are available with average power of 30 W or more. A moderate-power 5 W average power optically-pumped amplifiers have been operated to give pulses of 500 micro-Joules or more, as energy densities above the ablation threshold are needed for non-thermal ablation, and increasing the energy in such a system, increases the ablation rate in either depth or allows larger areas of ablation or both. The present invention, however, generally runs the optically-pumped amplifier with a time between pulses of a fraction (e.g., one-half or less) of the storage lifetime and uses a smaller ablation spot. Preferably, the spot is less than about 50 microns in diameter, but the diameter can be 60 or 75 microns and with sufficient power per amplifier, possibly even more (spot sizes herein are given as circle diameter equivalents, a "50 micron" spot has the area of a 50 micron diameter circle, but the spot need not be round). The smaller spot is preferably scanned to get a larger effective ablation area.

The present invention also preferably uses parallel optically-pumped amplifiers to generate a train of pulses to increase the ablation rate by further increasing the effective repetition rate (while avoiding thermal problems and allowing control of ablation rate by the use of a lesser number of operating optically-pumped amplifiers). The present invention may use a SOA preamplifier to amplify the initial pulse before splitting to drive multiple parallel optically-pumped amplifiers and another SOA before the introduction of the signal into each optically-pumped amplifier (which allows rapid shutting down of individual optically-pumped amplifiers). Further, the present invention generally operates with pulse energy densities at about three times the ablation threshold for greater ablation efficiency.

Although very-high power SOA's can be built, they are quite expensive and generally require large cooling systems. As a result, to be practical, an SOA generally needs somewhat lower power and a longer period of amplification, generally from 1 to 20 nanoseconds, and preferably between 5 and 20 nanoseconds. Air-grating compressors are impracticably large at these time periods, and thus the man-portable SOA amplifier systems use chirped fiber gratings (such gratings are commercially available from 3M). Fiber amplifiers could also use chirped fiber gratings, and generally these fiber gratings can be shorter, with less compression than those used with the SOAs.

The use of a 1 nanosecond selected-pulse with an optically-pumped amplifier and air optical-compressor (e.g., a Tracey grating compressor) typically gives compression with ~40% losses. At less than 1 nanosecond, the losses in a Tracey grating compressor are generally lower. If the other-than-compression losses are 10%, 2 nanoJoules are needed from the amplifier to get 1 nanoJoule on the target. Preferably, for safety purposes, 1550 nm light is preferably used. The use of much greater than 1 nanosecond selected-pulses in an air optical-compressor, in the past, presented two problems; the difference in path length for the extremes of long and short wavelengths needs to be more 3 cm and thus the compressor is large and expensive and generally not man-portable, and the losses increase with a greater degree of compression.

Ultra-short-pulse ablation can provide efficient material removal with very high ablation rates. Ablative removal of material is generally done with a sub-picosecond optical oscillator pulse that is stretched in duration, amplified, and then compressed. The optical amplifiers are generally power limited thus can give greater pulse energy at longer pulse durations, the compressor gives significant losses of pulse energy of per nanosecond of compression. Air-grating compressors can handle high power and while they can give multiple-nanosecond amplification in a reasonably small size by using multiple-pass configurations, but losses are greatly increased and little is gained. Thus usable pulse power is significantly limited.

This invention can provide a novel "no-pulse-energy-loss" air-grating-compressor configuration that gives a practical pulse compressor that compresses a pulse to sub-picosecond duration without reducing the energy of the pulse. It utilizes a single "active-grating" device that compresses and supplies energy to the pulse to at least make up for the inherent losses during the pulse compression. The active grating can be fabricated by placing a grating on the face of a novel low-gain active mirror.

Air-grating compressors typically bounce the beam between two gratings and use several reflections (e.g., 8) per pass and pulses lose some energy (e.g., 5%) in each reflection. Multiple-pass air-grating compressors also use at least one additional reflection between each pass. Thus such an 8-reflection single-pass grating would get ~66% of the input energy of the light out (0.95⁸) and the 34% loss/66% output gives losses of about 50% of the output. An 8-reflection active-grating device with similar reflection loss would get losses of about 40% of the output. A conventional two-pass 17-reflection grating would get ~42% of the input energy of the light out and gives losses of about 138% of the output. A 17-reflection two-pass active-grating device with similar reflection loss would get losses of about 85% of the output. In these two-pass configurations the active-grating losses are less than the output energy, while the conventional compressor heat-generating losses are significantly more than the output energy.

A conventional 35-reflection four-pass grating would get ~16.6% of the input energy of the light out and gives losses of about 502% of the output. A 35-reflection four-pass active-grating device with similar reflection loss would get losses of about 175% of the output. Thus, in these 35-reflection four-pass configurations, the active grating compressor reduces the losses by almost a factor of three. Even if a low-gain active mirror is used without a mirror and one conventional grating the losses are significantly reduced compared to the normal two grating compressor.

In order to handle the very high powers involved while avoiding amplifier overheating, ablative pulses have been created by generating ultra-short (e.g., sub-picosecond) pulses, stretching and amplifying the pulses, and then compressing the pulses back to an ultra-short duration. This is an improved way of performing the stretching and/or compressing that provides for higher efficiency, greater temporal stretching/compressing, and more accurate reduction to the original pulse duration in a package that is smaller, lighter, and less expensive.

This diffraction grating stretching/compressing method uses a tilted collimated input beam, spatial-spreading the beam, spatial-narrowing the beam, spatial-spreading the beam, spatial-narrowing the beam, and collimating the beam output, wherein the beam hits at least one of the gratings more than once (because of the tilt, the beam hits such a grating at a different line or point each time around).

Figure 2:
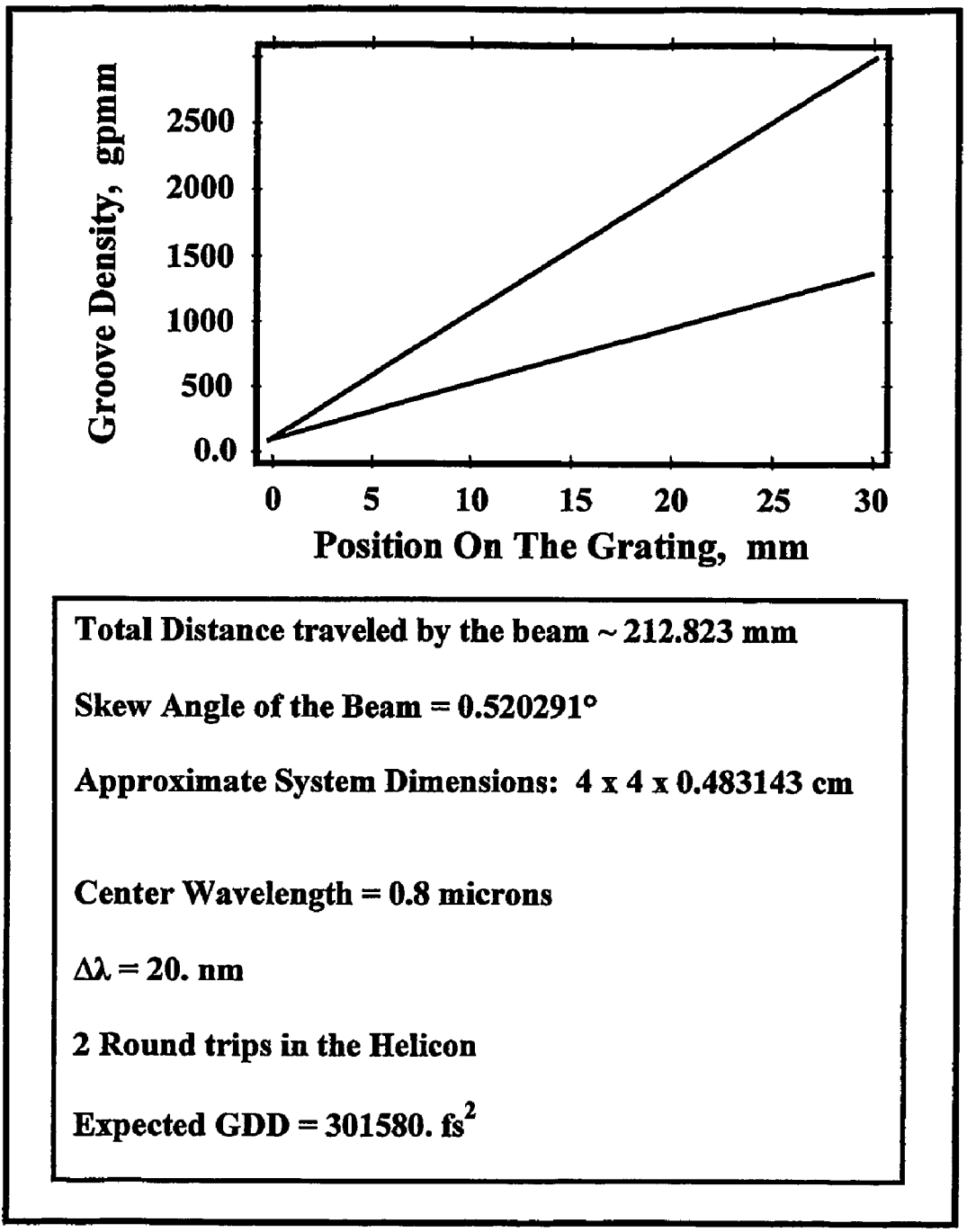
FIG. 2 shows a graph of grooves/mm vs. distance from the center axis and other design data for a helical path device.

In one embodiment, four transmission chirped gratings are used to diffract the beam in a generally helical path, such that the beam hits at least one of the gratings more than once (because of the tilt, the beam hits such a grating at a different point each time around). FIG. 1 shows a stretcher/compressor 10 in such an embodiment. The collimated beam of pulses 12 that are to be temporally modified (either stretched or compressed) comes from the left and enters the first grating 14 (almost perpendicularly; it has a slight upwards tilt). The first grating 14 diffracts the beam 16 at an angle toward the second grating 18 (maintaining the slight upwards tilt), which is at a right angle to the first grating 14. The first grating 14 also spatially spreads the beam (the beam 16 becomes wider in an essentially horizontal plane) as it travels from the first 14 to the second grating 16. The second grating 16 spatially compacts the beam back to about its original size, but due to the difference in path length of different wavelengths in a pulse, the pulse is either stretched or compressed. Here the beam goes twice around, hitting grating 14 three times and beam 20 exits stretcher/compressor 10 either temporally stretched or compressed. The design specifications are shown in FIG. 2, including the groove density as a function of position on the grating (in groves per mm, or gpmm). The gratings are shown (not to scale and only a few grooves are shown; but the varying spacing of the grooves is indicated) on FIG. 3. While 3 of the gratings are the same, the 4-th grating has an input and output portions (e.g., the input portion on the bottom and the output portion on the top) that have twice the groove spacings of the middle portion. The middle portion of the 4-th grating has the same spacings as the other 3 gratings. As can be seen from FIG. 1, only portions of the gratings are used, and the gratings need not extend to meet at the center axis. For 99% diffraction efficiency per grating, total efficiency of the device is 91%. This example has two complete turns and with a 20 nm pulse spectral width gives about 40 ps of stretching/compressing. With about twice the size and 25 turns, this type of device can give about 1 ns of stretching/compressing, with reasonable efficiency.

FIG. 2 shows a graph of grooves/mm vs. distance from the center axis and other design data for a helical path device of FIG. 1. In FIG. 1, the total distance traveled by the beam is ~212.823 mm; the skew angle of the beam is 0.520291o the approximate system dimensions: 4×4×0.483143 cm; the center wavelength=0.8 microns; delta-lambda=20 nm; there were 2 round trips and the expected GDD=301580 fs2.

Figure 3:
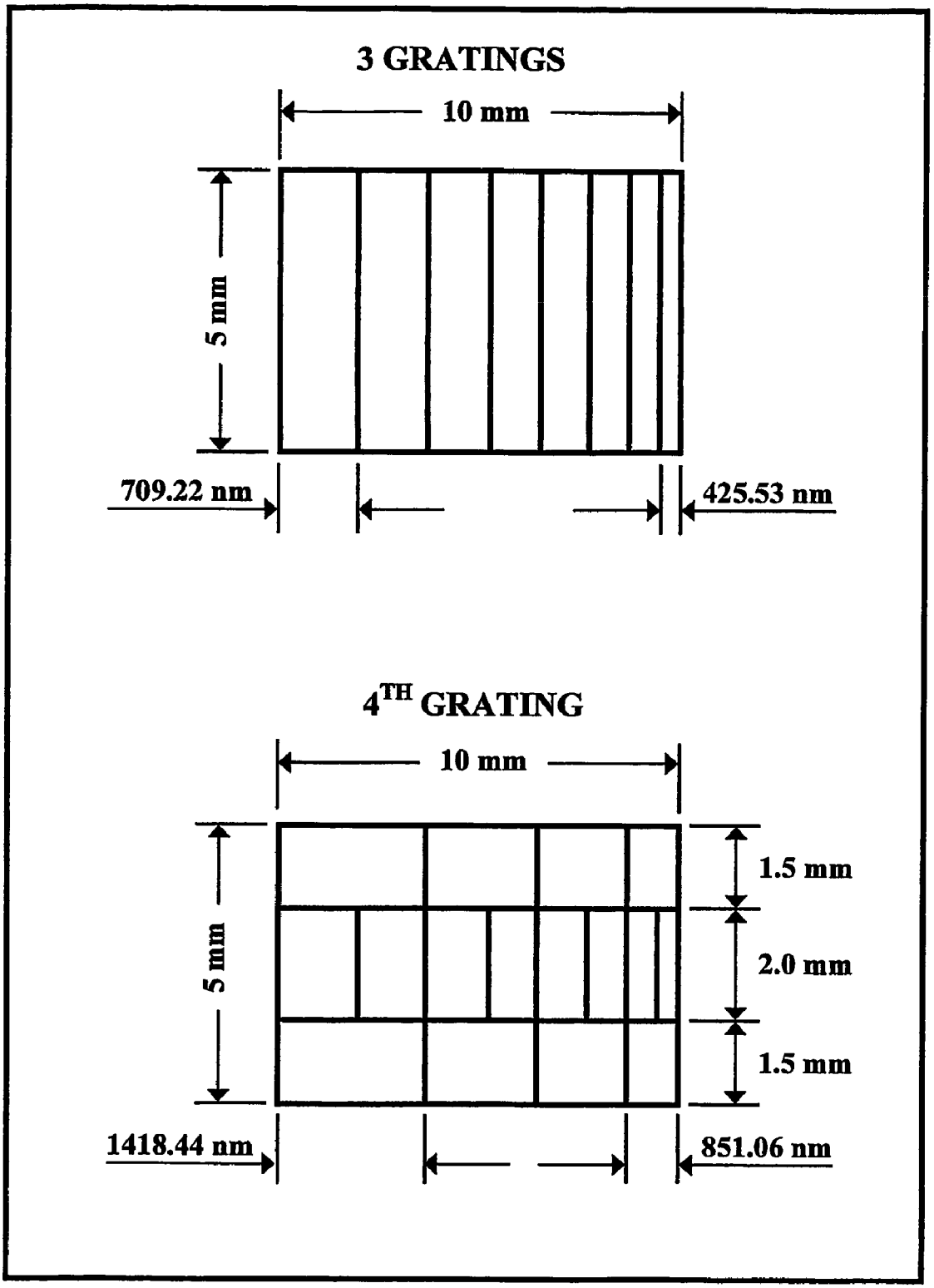
FIG. 3 shows gratings for a helical path device.

FIG. 3 shows gratings for a helical path device of FIG. 1. A device having similar transmissive gratings disposed at right angles is shown in FIG. 4 of U.S. Pat. No. 5,822,097 by Tournois, which also gives different pathlengths to different wavelength. Tournois, however, uses an input/spatial-spreading grating, spatial-narrowing grating and a collimating output grating and thus he uses a single spatial-spread and spatial-narrowing of the beam. The dimensions of such a device have to be quite large for considerable pulse stretching/compression thus making it impractical. In addition, the an incoming beam is perpendicular to the input grating and all rays of light stay in a single plane, thus making it impossible to use such a device in a multi-pass configuration to obtain higher stretching/compression factors.

In the embodiment of FIG. 4, two reflective gratings 34, 38 are used in a right angle configuration of stretcher/compressor 30. The gratings separation is 127.8 mm (about 5 inches). The collimated beam of pulses 32 that are to be temporally modified (either stretched or compressed) enters the first grating 34 (almost perpendicularly; it has a slight upwards tilt). The first grating 4 diffracts the beam 36 at an angle toward the second grating 38 (maintaining the slight upwards tilt), which is perpendicular to the first grating 4. The first grating 34 also spatially spreads the beam (the beam 36 becomes wider in an essentially horizontal plane) as it travels from the first 34 to the second grating 38. The second grating 38 spatially compacts the beam back to about its original size, but due to the difference in path length of different wavelengths in a pulse, the pulse is either stretched or compressed. Here the beam goes back and forth four times, hitting grating 34 six times and grating 38 four times and beam 40 exits stretcher/compressor 30 either temporally stretched or compressed. After the two double-passes before the prism, the beam has a spatial chirp as a result of the tilt. A prism is used to flip the beam, preserving the tilt angle, and reversing the chirp direction. The chirp is then corrected by the successive two double-passes. The output beam thus has no spatial chirp and is collimated. For the 1 degree tilt, the apex angle has to be equal to 90 degrees 40 minutes.

Figure 5:
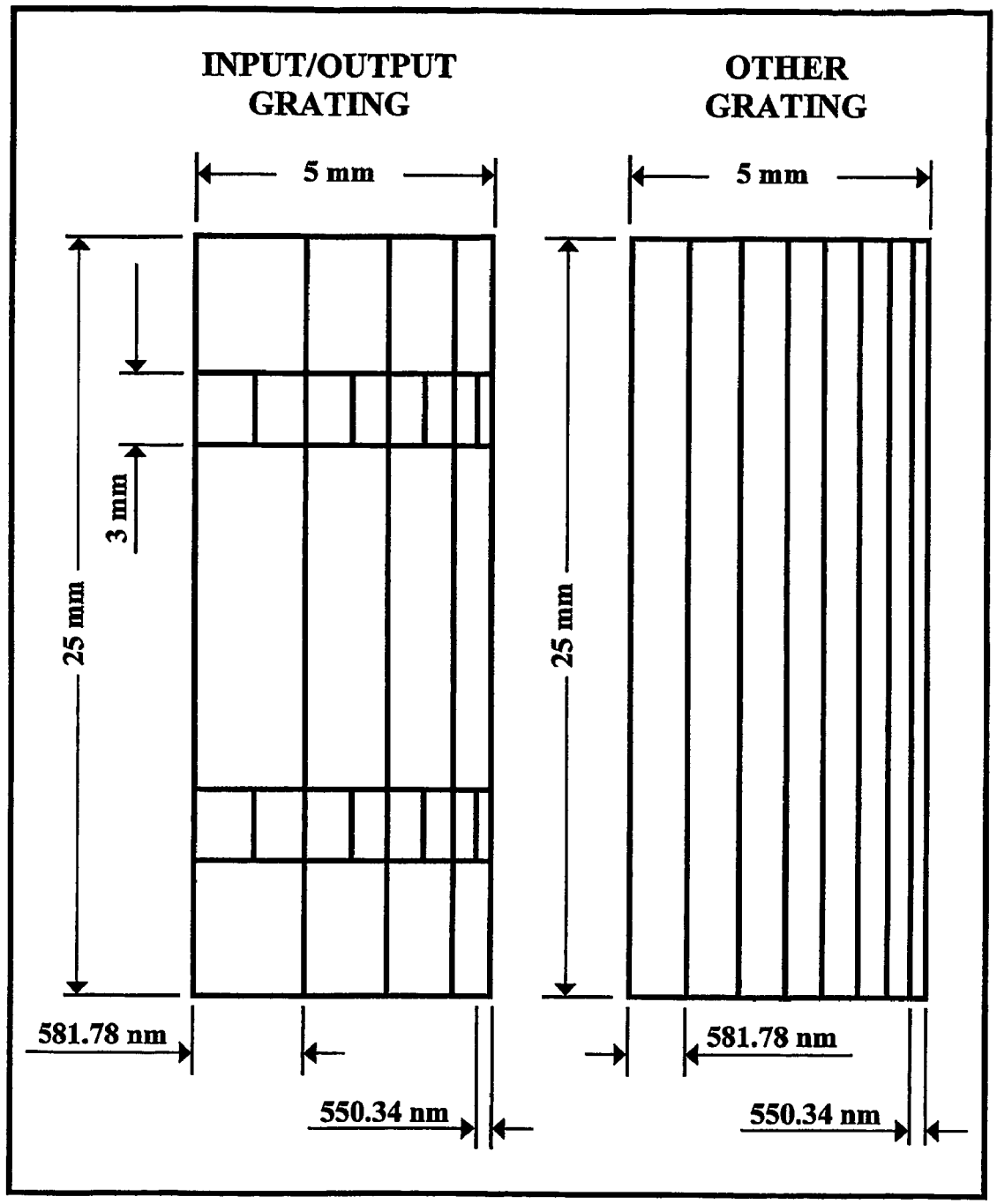
FIG. 5 shows gratings for the reflective chirped gratings device.
Figure 6:
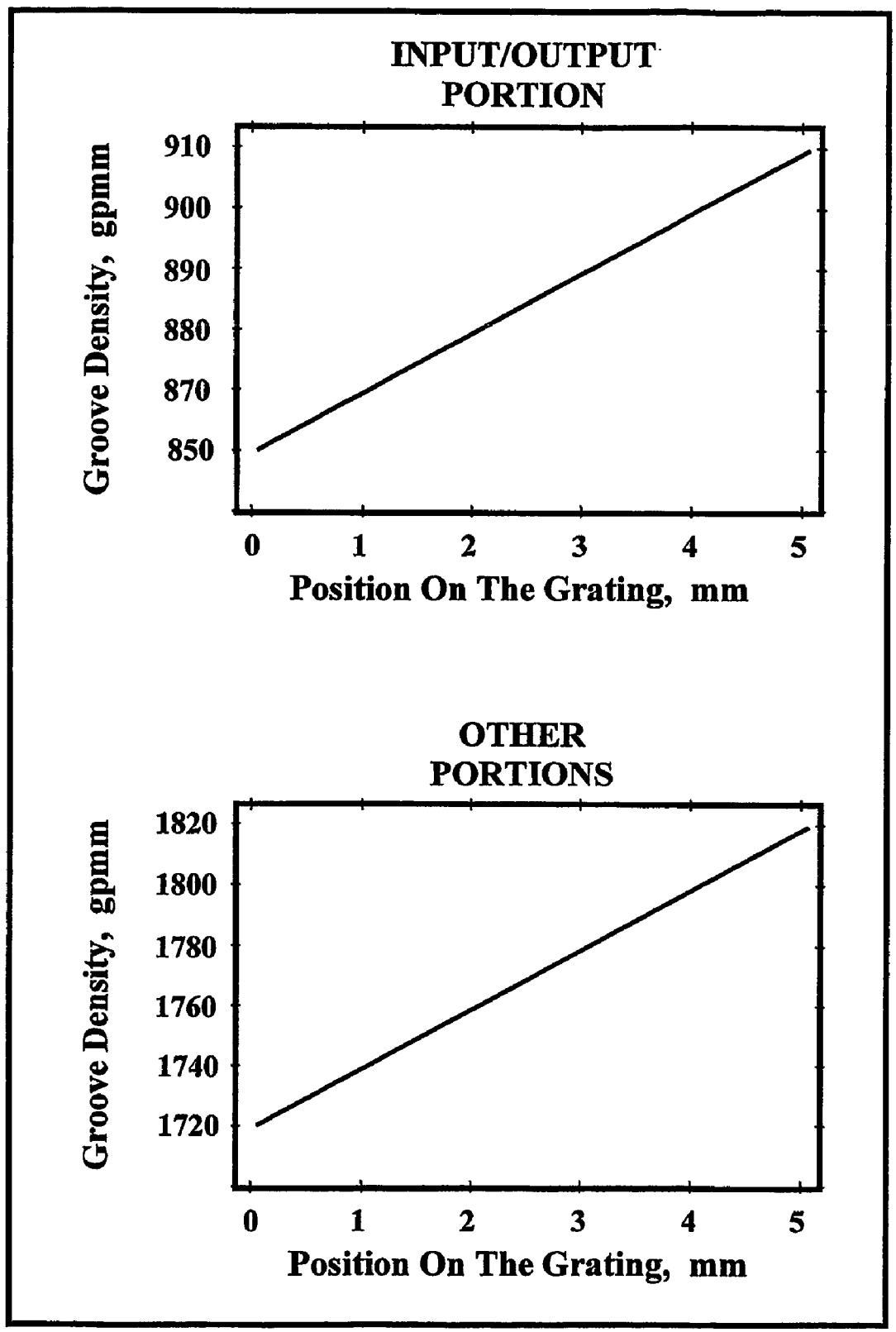
FIG. 6 shows groove density in grooves/mm vs. position on the grating for the reflective chirped gratings device.

The gratings of this embodiment are shown in FIG. 5. The groove density as a function of position on the grating is shown in FIG. 6. Grating height (along the grooves) depends on the tilt angle and for a 1 degree tilt, grating height is about 25 mm (1 inch). Grating width depends on the gratings separation and is less than 5 mm in the illustrated configuration. The performance of this embodiment is similar to that of the helical path embodiment. Note that here the beam centerline is in one plane and the rays are fanned out into multiple different planes that are perpendicular to the beam centerline plane.

Figure 7:
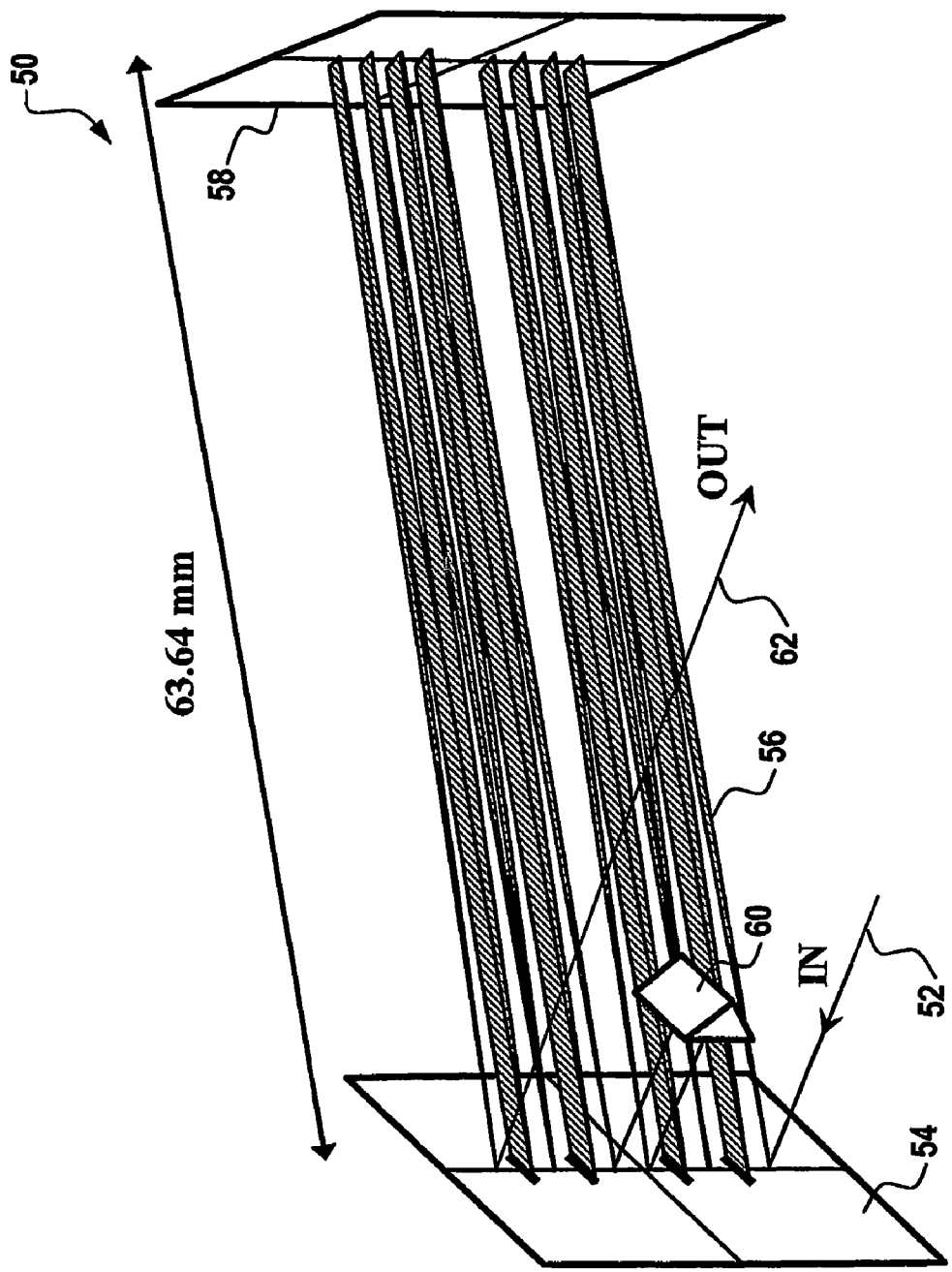
FIG. 7 shows an isometric of a compact reflective device using one reflective chirped grating and one mirror and a retro-reflector for spatial-chirp correction.

In the embodiment of FIG. 7, one reflective grating and one mirror are used in a 45-degree angle configuration. The device length is reduced by a factor of 2 (down to 2.5 inches). The collimated beam of pulses 52 that are to be temporally modified (either stretched or compressed) enters grating 54 (almost perpendicularly; it has a slight upwards tilt). The first grating 54 diffracts the beam 56 at an angle toward a mirror 58 (maintaining the slight upwards tilt). The grating 54 also spatially spreads the beam (the beam 56 becomes wider in an essentially horizontal plane) as it travels from grating 54 to the mirror 58. The beam continues to widen after being reflected by the mirror. The second hit on grating 54 spatially compacts the beam back to its original size (after the second reflection off mirror 58), but due to the difference in path length of different wavelengths in a pulse, the pulse is either stretched or compressed. Here a prism 60 is used to correct spatial chirp. The spatial chirp introduced during the four round-trips is equal and opposite in sign to the spatial chirp acquired during the next four round-trips. The output beam thus has no spatial chirp and is collimated. Here the beam goes back and forth multiple times, hitting the grating 54 ten times and mirror 58 eight times and beam 62 exits stretcher/compressor 50 either temporally stretched or compressed.

In such an embodiment, fabrication cost and time are reduced, as there is just one grating to make. The alignment is significantly simpler, as one just needs to make sure the grating and the mirror are at 45 degrees and the mirror is perpendicular to rays (at an angle equal to the beam tilt angle, to be exact). The mirror dimensions are 25 mm×5 mm and the mirror can be an active mirror. The grating height (along the grooves) again depends on the tilt angle, here, with the 1 degree tilt, the grating height is 25 mm (1 inch), and the grating width depends on the separation between the grating and the mirror and is less than 5 mm. A retro-reflector (prism or a mirror pair) is again used to compensate for a spatial chirp of the output beam, resulting from the tilt (for 1 degree tilt the apex angle is equal to 90 degrees 40 minutes).

Figure 8:
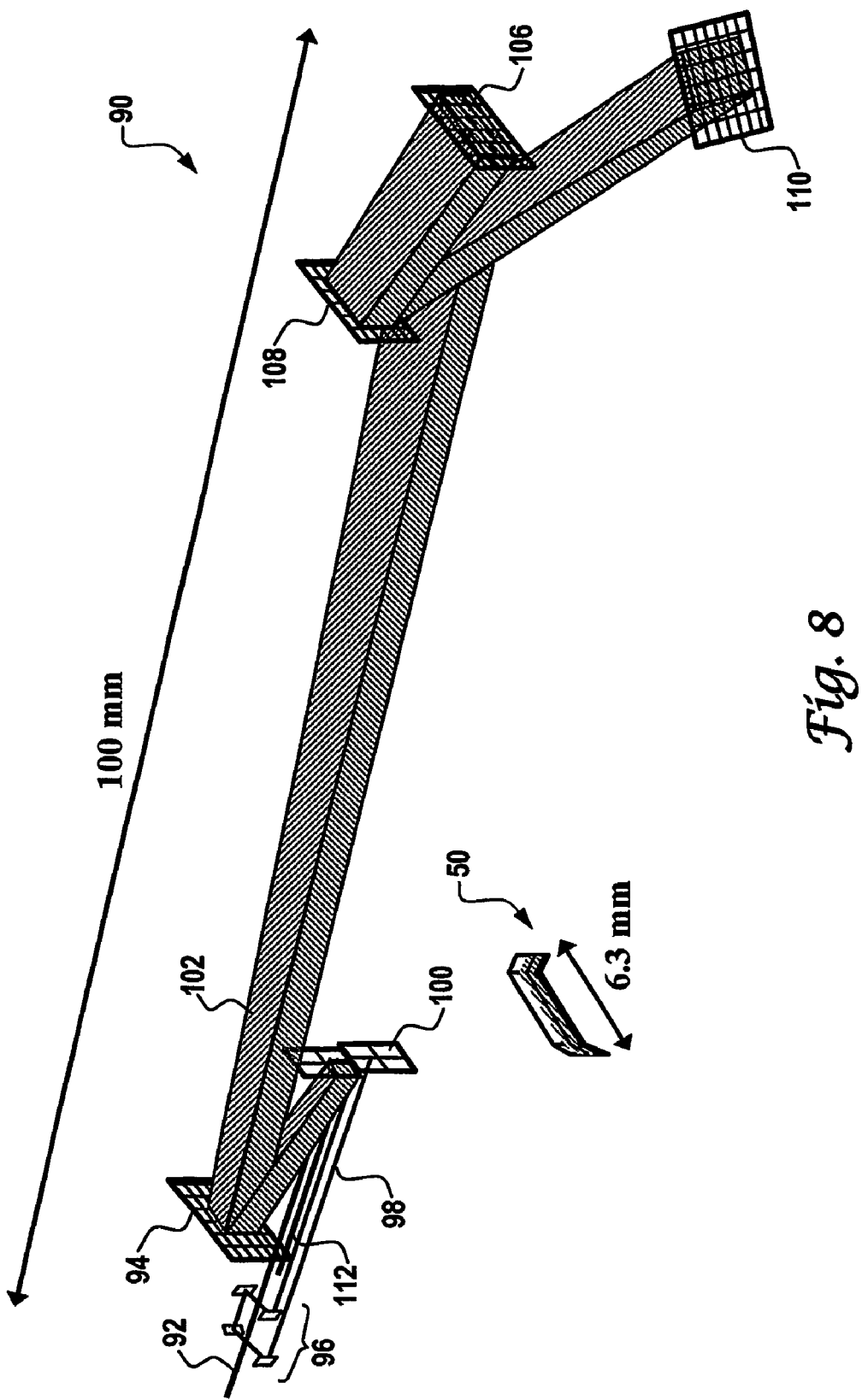
FIG. 8 is an isometric (approximately to scale) comparing the size of a traditional stretcher/compressor with the compact design of FIG. 7.

FIG. 8 shows size comparison between this compact design and a traditional stretcher. In a conventional stretcher/compressor 90, the beam 92 enters and is reflected and spatially broadened by grating 100, then off grating 94, then off grating 106, then off grating 108, and then off grating 110. Grating 110 reverses the direction and also begins the spatial narrowing of the beam. After reflecting off grating 100 for the second time, beam 98 goes to chirp corrector 98, and exits. The length 108 of a conventional stretcher/compressor 90 is 100 cm (one meter) versus the 6.36 cm length 50 of our stretcher/compressor 50 of FIG. 7. The length of the conventional unit is over 15 times longer.

Figure 9:
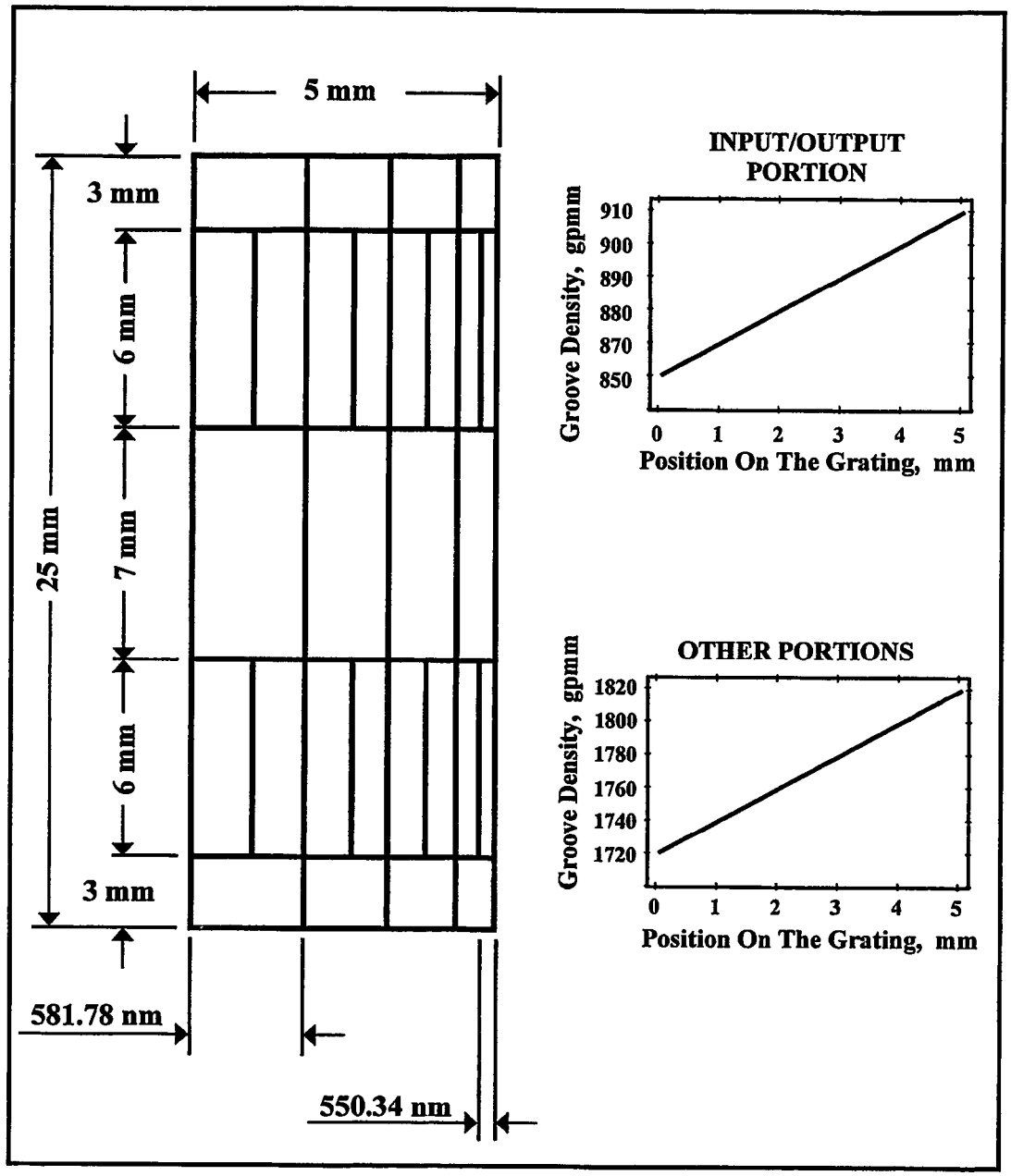
FIG. 9 shows gratings and groove density in grooves/mm vs. position on the grating for the single reflective chirped grating device of FIG. 7.

FIG. 9 shows a grating and groove density as a function of position on the grating for the embodiment of FIG. 7. As compared to the two reflective grating device, the one reflective grating and one mirror device does have a decrease in efficiency due to losses at the mirror, which at the current state of mirror fabrication technology is not a big impediment. Note that here the beam centerline is also in one plane and the rays are also fanned out into multiple different planes that are perpendicular to the beam centerline plane.

Figure 10:
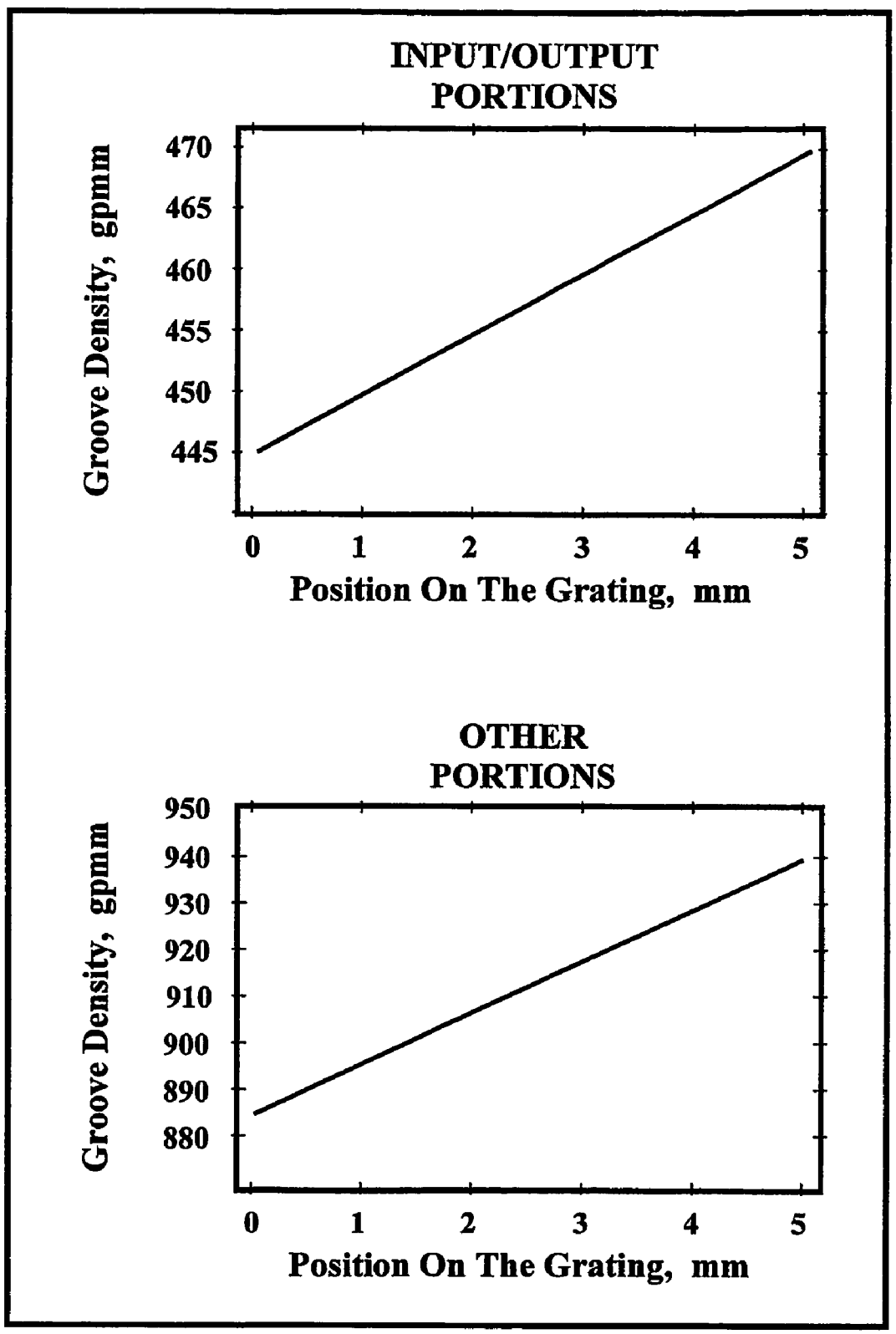
FIG. 10 shows groove density in grooves/mm vs. position on the grating for two reflective chirped grating device or one reflective chirped grating and one mirror device operating with a 1550 nm beam (as opposed to the designs above for a 800 nm beam)
Figure 11:
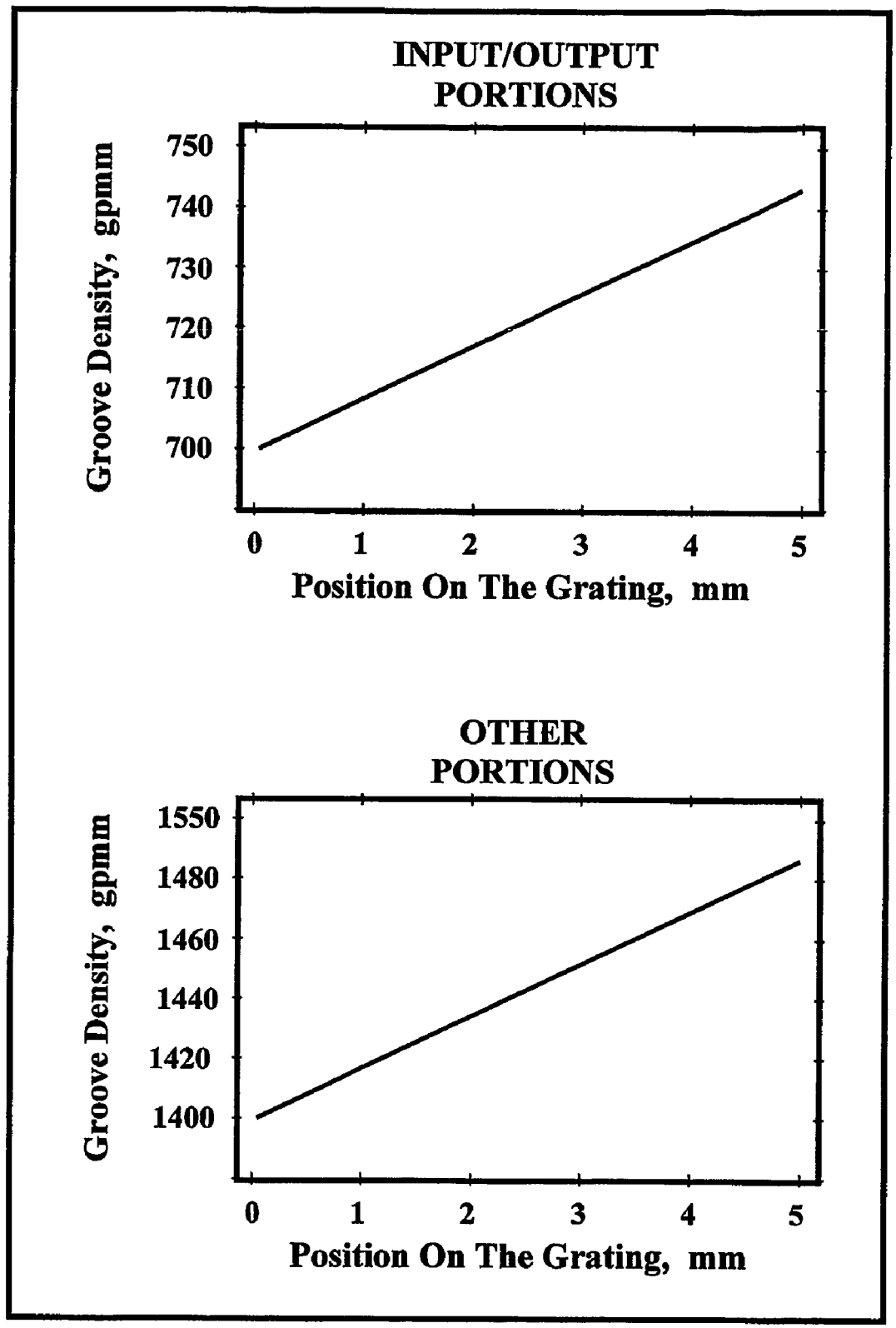
FIG. 11 shows groove density in grooves/mm vs. position on the grating for two reflective chirped grating device or one reflective chirped grating and one mirror device operating with a 980 nm beam (as opposed to the designs above for a 800 nm beam)

The groove densities as a function of position on the grating for the embodiment FIG. 1-9 are for 800 nm devices. FIG. 10 shows groove density as a function of position on the grating for 1550 nm embodiments (input/output grating graph shown above and other grating graph shown below). FIG. 11 shows groove density as a function of position on the grating for 980 nm embodiments (input/output grating graph shown above and other grating graph shown below).

This technique can be used for either stretching or compressing, but is preferably used for compressing. Another alternative is generating a wavelength-swept-with-time initial pulse for the optically-pumped pulse amplifier input and compressing (thus compressing without using a stretcher). At 1550 nm compression is much more efficient than at shorter wavelengths. With longer distances between elements and/or more diffractions, higher stretching/compression factors can be obtained, for example operation with a 10 nanosecond stretch/compression or more may be possible.

Note that electrically-pumped semiconductor optical amplifiers or optically-pumped optical pulse amplifiers in general (including, and in such shapes as slabs, discs, and rods) can be used. In some embodiments, the mirror is an active mirror, and diode pump-current may be used to control the amplification of the active mirror.

While slab lasers of single-crystal or glass have been used in the past, they have used an amplified beam passing through one of the long direction of the slab, not the smallest dimension of the slab. While more than one slab laser have been used in series in the past, the slabs have not been aligned as here. In the past, lasers have used a variety of dopants including chromium, and titanium doping in crystals (e.g. alexandrite or sapphire), and neodymium and europium doping in glass. Cr:YAG or europium (or europium/ytterbium) doped glass is preferably used to give a eye-safe wavelength preferred for safety reasons. The superior cooling of the present invention allows the use of an inexpensive glass matrix even at relatively high power.

This high-power-optical-amplifier uses a number of spaced, thin slabs (e.g. disc-shaped doped-slabs that are stacked, with a space between discs), aligned to give an amplifier both with a high active cross-section and a very high surface area to volume ratio. Further the internal reflections are controlled to give high efficiency. The eye-safe laser beam being amplified is passed through the thin dimension of the slabs and the beam travels through surfaces that have very low reflectivity, as the surface reflectivity is reduced either by the surfaces being placed near the Brewster angle with respect to the polarized beam and/or by use of surface A/R coatings (preferably both). Further, all slab surfaces within the amplifier are generally slightly non-parallel (including opposing surfaces of the slabs, as well as surfaces of other slabs) to reduce lasing of reflections and increase efficiency.

Cooling gas can pass between the slabs and provide exceptionally good heat transfer not only because of the high surface area but also because of the very short distance the heat has to travel to reach the surface of the thin slabs. To still further increase system effectiveness, ablative sub-ten-picosecond pulses are generally used. To give an eye-safe wavelength (wavelengths longer than about 1400 nm) for safety reasons, Cr:YAG is preferably used, but in some embodiments europium (or europium/ytterbium) doped glass is used as the superior cooling of the present invention allows use even of an inexpensive glass matrix. As some system components are generally glass and absorption of light in glass is high above about 1800 nm, the system is preferably operated between 1400 and 1800 nm.

Figure 12:
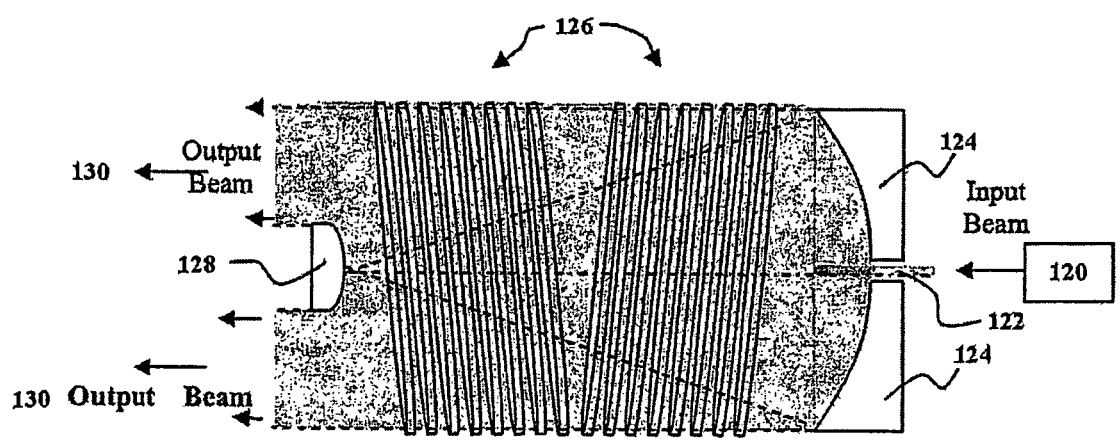
FIG. 12 shows an amplifier with two sets of four slabs, and the sets slanted in opposite directions.

FIG. 12 shows an amplifier 120 with two sets 122, 124 of four slabs, and the sets 122, 124 slanted in opposite directions. The polarized input beam 16 passes through the first set 122 and exits the second set 14 as an amplified beam 128. The slabs have two surfaces approximately perpendicular to a thickness dimension, and are aligning with surfaces approximately parallel to, and spaced from adjacent slabs. The slab surfaces are rendered essentially non-reflective by being placed at about the Brewster angle with respect to the polarized optical input beam 126. The slabs are shown with surfaces of adjacent slabs approximately parallel, and surfaces of each slab being approximately parallel. Preferably, however, no two of the surfaces within the amplifier are parallel and small (e.g. 0.1 degree, 0.4 degree or even 1 degree) angular offsets are used to assure that perfectly parallel surfaces are avoided. Thus the slabs are slightly wedge-shaped and the spaces between the slabs are slightly wedge-shaped (too slight to be effectively shown in the drawing). As used herein, the term "opposed" when used in describing slab surfaces, means the surfaces approximately perpendicular to the smallest dimension, and includes surfaces that are not parallel. Thus it includes two flat surfaces of a disc that are slightly out of parallel. Note that in most preferred embodiments, the two surfaces are not exactly parallel to each other, and thus the beam is hitting at least one of the surfaces at an angle other than precisely the Brewster angle (generally being, however within about 1 degree of the Brewster angle).

Preferably the beam is polarized and the beam is about at Brewster angles to the surfaces. When the surfaces of a disc are not precisely parallel, the beams entering and exiting a disc are not precisely parallel. The terms "perpendicular" and "substantially perpendicular" as used herein means within one degree of perpendicular. The term "precisely perpendicular" as used herein means within one-tenth of a degree of perpendicular. The term "parallel" as used herein with regards to surfaces means the surfaces have perpendiculars within one degree of being parallel. The term "precisely parallel" as used herein with regards to surfaces means the surfaces have perpendiculars means within one-tenth of a degree of perpendicular.

Note that an experimental multiple disk laser called the Heat Capacity Laser has been used for testing laser machining in a laboratory. This laser, however, did not teach or suggest, the use of practical eye-safe wavelengths, sub-ten-picosecond ablation, or the avoiding of parallel surfaces within the amplifier. Further, its efficiency was very low, and after running for less than 2 minutes, it needed to be turned off to cool for about 3 hours and thus it was clearly not a practical system.

The active grating can be fabricated by placing a grating on the face of a novel low-gain active mirror. In one embodiment, this low-gain active mirror has a gain of only two or three, compared to the very high pulse energy conventional active mirrors that gains of thousands (see U.S. Pat. No. 6,339,605 entitled "Active mirror amplifier system and method for a high-average power laser system" and U.S. Pat. No. 6,610,050 entitled "Laser beam delivery system with multiple focal points").

The '605 patent describes an active-mirror system (figure numbers deleted) as follows: "typically, the laser gain medium disk may have a thickness ranging approximately from 1 mm to 10 mm and transverse dimensions ranging from about 10 mm to 300 mm. The material of the laser gain medium disk comprises a suitable solid-state laser gain medium such as, but not limited to neodymum doped yttrium aluminum garnet (Nd:YAG), yitterbium doped yttrium aluminum garnet (Yb:YAG), neodymum chromium codoped gadolinium gallium garnet (Nd:Cr:GGG or "GGG" for short), or neodymum doped glass (Nd:Glass).

"Referring further to FIGS., the back planar surface has a dielectric optical coating with high reflectivity at a laser wavelength and at optical pump wavelengths. The front surface has a dielectric optical coating that is antireflective at the laser wavelength and at the optical pump wavelength. The back surface is in contact with a surface of a cooled, rigid substrate. The surface contains an array of interconnected vacuum microchannels extending generally over, but not beyond, the contact area between the disk and the substrate."

The '050 patent describes a active mirror system in which a master beam produced by the laser source is directed into a lenslet array to partition the master beam into a plurality of beams, with each of the beams having a separate focal point. In one embodiment of the '050 patent, the lenslets are on an active mirror.

In one embodiment, the active grating of the present invention uses two novel low-power, low-gain active mirrors with Cr:YAG gain media, and with the mirror backsides directly air-cooled. The grating can be etched in the front surface using known semiconductor fabrication lithographic techniques. As in conventional grating compressors, the beam will be fanned out into a broad beam and then focused back into a narrow beam, with different wavelengths having different path lengths and thus different time delays (such that the spreading in time introduced in the stretching is generally eliminated).

In an alternate embodiment of the present invention, one low-gain active mirror with a surface grating and one conventional grating is used. In still another alternate embodiment, one low-gain active mirror without a surface grating and one conventional grating is used.

Note that the active mirror can be controlled by repetition rate and/or diode-pumping current in the manner described (generally using fiber amplifiers as examples) in co-pending provisional applications cited below. Note further that lamp-pumped optical amplifiers can be controlled by controlling lamps in a manner similar to that of controlling pump diode current. Preferably, diode pump-current is used to control the amplification of the active mirror. Generally optical pump device (diode or lamp) current is controlled either directly or indirectly by controlling voltage, power, and/or energy. As used herein, controlling current can include shutting off one or more optical pump devices, when multiple pump devices are used.

The alternate configuration with a semiconductor optical amplifier (SOA) and a with a chirped fiber compressor, and with pulses stretched to 1 to 20 nanosecond during amplification is run at repetition rates with a time between pulses of more that the very short semiconductor storage lifetime. Preferably the present invention uses a semiconductor generated initial pulse. The present invention may use a SOA preamplifier to amplify the initial pulse before splitting to drive multiple amplifiers. The present invention preferably scans the ablation a smaller spot to get a larger effective ablation area, and in many cases the scanned spot is smaller than the above optically-pumped-amplifier case. In addition, the present invention preferably uses parallel amplifiers to generate a train of pulses to increase the ablation rate by further increasing the effective repetition rate (while avoiding thermal problems and allowing control of ablation rate by the use of a lesser number of operating amplifiers).

Generally the present invention operates with pulse energy densities at about three times the ablation threshold for greater ablation efficiency. The system can be run either with dynamic feedback from measurement of pulse energy with a control point being varied for materials of different ablation thresholds, or open-loop. The open-loop control could be a selector switch where the selector switch is used to directly or indirectly select a repetition rate. The selector switch could be a multi-position switch, but could also be a high/low switch.

The use more than one amplifier in parallel train mode (pulses from one amplifier being delayed to arrive one or more nanoseconds after those from another amplifier) allows step-wise control of ablation rate independent of pulse energy. At lower desired powers, one or more amplifiers can be shut off (e.g., the optical pumping to a optically-pumped amplifier), and there will be fewer pulses per train. Thus with 20 amplifiers there would be a maximum of 20 pulses in a train, but most uses might use only three or four amplifiers and three or four pulses per train. While CW operation might normally be used for operating amplifiers, amplifiers might be run for e.g., one second and then turned off and a dormant amplifier turned on to spread the heat load.

Generally the fiber amplifiers are optically-pumped CW (and are amplifying perhaps 100,000 times per second in 1 nanosecond pulses). Alternately, non-CW-pumping might be used in operating amplifiers, with amplifiers run in a staggered fashion, e.g., one on for a first half-second period and then turned off for a second half-second period, and another amplifier, dormant during the first-period, turned on during the second period, and so forth, to spread the heat load.

In such systems, the present invention can control input optical signal power, optical pumping power of optically-pumped amplifiers, timing of input pulses, length of input pulses, and timing between start of optical pumping and start of optical signals to control pulse power, and average degree of energy storage in optically-pumped amplifier.

Many fiber amplifiers have a maximum power of 4 MW, and thus a 10-microJoule-ablation pulse could be as short as 2 picoseconds. Thus e.g., a 10 picosecond, 10 microJoule pulse, at 500 kHz (or 50 microJoule with 100 kHz), and, if heating becomes a problem, operating in a train mode and switching fiber amplifiers. Thus one might rotate the running of ten fiber amplifiers such that only five were operating at any one time (e.g., each on for $\frac{1}{10}^{th}$ of a second and off for $\frac{1}{10}^{th}$ of a second). Again one can have ten fiber amplifiers with time spaced inputs, e.g., by 1 nanosecond, to give a train of one to 10 pulses. With 5 W amplifiers operating at 100 kHz (and e.g., 50 microJoules) this could step between 100 kHz and 1 MHz. With 50% post-amplifier optical efficiency and 50 microJoules, to get 6 J/sq. cm on the target, the spot size would be about 20 microns.

Another alternative is to have 20 optically-pumped amplifiers with time spaced inputs, e.g., by 1 nanosecond, to give a train of one to 20 pulses. With 5 W amplifiers operating at 50 kHz (and e.g., 100 microJoules) this could step between 50 kHz and 1 MHz. With 50% post-amplifier optical efficiency and 100 microJoules, to get 6 J/sq. cm on the target, the spot size would be about 33 microns. The selected pulse might be 50 to 100 picoseconds long. A similar system with 15 optically-pumped amplifiers could step between 50 kHz and 750 kHz.

Another alternative is to have 10 optically-pumped amplifiers with time spaced inputs, e.g., by 1 nanosecond, to give a train of one to 20 pulses. With 5 W amplifiers operating at 20 kHz (and e.g., 250 microJoules) this could step between 20 kHz and 200 kHz. With 50% post-amplifier optical efficiency and 250 microJoules, to get 6 J/sq. cm on the target, the spot size would be about 50 microns. The selected pulse might be 100 to 250 picoseconds long. A similar system with 30 optically-pumped amplifiers could step between 20 kHz and 600 kHz.

Generally it is the pulse generator that controls the input repetition rate of the optically-pumped amplifiers to tune energy per pulse to about three times threshold per pulse.

Another alternative is generating a sub-picosecond pulse and time-stretching that pulse within semiconductor pulse generator to give the wavelength-swept-with-time initial pulse for the fiber amplifier. Another alternative is to measure light leakage from the delivery fiber to get a feedback proportional to pulse power and/or energy for control purposes. Measurement of spot size, e.g., with a video camera, is useful, and can be done with a stationary spot, but is preferably done with a linear scan. Preferably, the spot is less than about 50 microns in diameter.

The camera is preferably of the "in-vivo" type using an optical fiber in a probe to convey an image back to, e.g., a vidicon-containing remote camera body. This is especially convenient with a handheld beam-emitting probe and can supply its own illumination. Other cameras using an optical fiber in a probe to convey an image back to a remote camera body, e.g., a vidicon-containing camera with a GRIN fiber lens, can also be used. Endoscope type cameras can also be used.

Smaller ablation areas may be scanned by moving the beam without moving the probe. Large areas may be scanned by moving the beam over a first area, and then stepping the probe to second portion of the large area and then scanning the beam over the second area, and so on. The scanning may be by beam deflecting mirrors mounted on piezoelectric actuators. Preferably the system actuators scan over a larger region but with the ablation beam only enabled to ablate portions with defined color and/or area. A combination of time and, area and/or color, can be preset, e.g., to allow evaluation after a prescribed time.

Ablative material removal is especially useful for medical purposes either in-vivo or on the body surface and typically has an ablation threshold of less than 1 Joule per square centimeter, but may occasionally require surgical removal of foreign material with an ablation threshold of up to about 2 Joules per square centimeter. The use of more than one amplifier in parallel train mode (pulses from one amplifier being delayed to arrive one or more nanoseconds after those from another amplifier. At lower desired powers, one or more amplifiers can be shut off (e.g., the optical pumping to a fiber amplifier), and there will be fewer pulses per train. Thus with 20 amplifiers there would be a maximum of 20 pulses in a train, but most uses might use only three or four amplifiers and three or four pulses per train. While CW operation might normally be used for operating amplifiers, amplifiers might be run for e.g., one second and then turned off and a dormant amplifier turned on to spread the heat load.

The present invention also provides a method of system operation for material removal from a body portion being ablated by optical-ablation with controlled pulse energy from an amplifier by utilizing an optical oscillator in the generation of a series of wavelength-swept-with-time pulses, wherein the system has a repetition rate that gives a time between pulses of less than ½ the storage time of the fiber amplifier, amplifying the wavelength-swept-with-time pulse with the fiber-amplifier, controlling pulse energy of the fiber-amplifier pump diodes to give a pulse energy density applied to the body of between 2.5 and 3.6 times ablation threshold of the body portion being ablated, and time-compressing the amplified pulse and illuminating a spot on a portion of an object with the time-compressed optical pulse, wherein the system has a spot size between 10 and 60 microns diameter.

In addition, the present invention provides a method of surgical material removal from a body by optical-ablation with controlled pulse energy from a fiber amplifier by inputting a nominal spot size signal and a pulse-energy-for-material-being-ablated signal, utilizing an optical oscillator in the generation of a series of wavelength-swept-with-time pulses, primarily controlling pulse energy based on the pulse-energy-for-material-being-ablated signal by either selecting pulses from the oscillator generated series of wavelength-swept-with-time pulses, wherein the fraction of pulses selected can be controllably varied to give a selected pulse repetition rate that is a fraction of the oscillator repetition rate, or passing electrical current through at least one pump diode to generate pumping light, optically pumping the fiber amplifier with the pumping light, and controlling pump diode current, using an ablation spot-size sensor to measure the ablation spot size and dynamically adjusting either the fraction of pulses selected or the pump diode current for changes in ablation spot size from the nominal spot size; amplifying the wavelength-swept-with-time pulse with the fiber-amplifier, and time-compressing the amplified pulse and illuminating a portion of the body with the time-compressed optical pulse, whereby controlling the pulse selection controls the pulse energy.

Furthermore, the present invention provides a method of system operation for surgical material removal from a body by optical-ablation with controlled pulse energy from a fiber amplifier by determining a size of a spot to be used by the system, wherein the spot is between 10 and 60 microns diameter; setting a repetition rate to give time between pulses of between ½ and $\frac{1}{10}^{th}$ the storage time of the fiber amplifier into the system, inputting a pulse-energy-for-material-being-ablated signal into the system; controlling current through one or more fiber-amplifier pump diodes to give a pulse energy density applied to the body is between 2.5 and 3.6 times ablation threshold of the body portion being ablated, utilizing an optical oscillator in the generation of a series of wavelength-swept-with-time pulses, amplifying the wavelength-swept-with-time pulse with the fiber-amplifier, time-compressing the amplified pulse and illuminating the spot on a portion of the body with the time-compressed optical pulse; and scanning the spot over an area, whereby removal over the area is even due to the high repetition rate, while the pulse energy is at a near optimum efficiency level. Preferably the fiber-amplifier repetition rate is at least 0.6 million pulses per second. Preferably the ablation spot size is between 20 and 50 microns in diameter. In some preferred embodiments, the ablation spot size is between 20 and 40 microns in diameter.

Moreover, the present invention provides a method of surgical material removal from a body by optical-ablation with controlled pulse energy from a optically-pumped pulse amplifier by inputting a nominal spot size signal and a pulse-energy-for-material-being-ablated signal, utilizing an optical oscillator in the generation of a series of wavelength-swept-with-time pulses, primarily controlling pulse energy based on the pulse-energy-for-material-being-ablated signal by either selecting pulses from the oscillator generated series of wavelength-swept-with-time pulses, wherein the fraction of pulses selected can be controllably varied to give a selected pulse repetition rate that is a fraction of the oscillator repetition rate, or passing electrical current through at least one pump diode to generate pumping light, optically pumping the optically-pumped pulse amplifier with the pumping light, and controlling pump diode current; using an ablation spot-size sensor to measure the ablation spot size and dynamically adjusting either the fraction of pulses selected or the pump diode current for changes in ablation spot size from the nominal spot size, amplifying the wavelength-swept-with-time pulse with the fiber-amplifier, and time-compressing the amplified pulse and illuminating a portion of the body with the time-compressed optical pulse, whereby controlling the pulse selection controls the pulse energy.

The present invention also provides a method of ablative material removal, from a surface or with a short optical pulse that is amplified and then compressed by generating an initial pulse in a pulse generator within a man-portable system, amplifying the initial pulse and then compressing the amplified pulse within the man-portable system, wherein the amplifying and compression are done with either a fiber-amplifier and a 10 picosecond-1 nanosecond pulse-compressor combination, or a SOA and chirped fiber compressor combination, and applying the compressed optical pulse to the surface.

The amplifying and compressing can be done with a fiber-amplifier and air-path between gratings compressor combination, e.g., with the oscillator pulses of between 10 picoseconds and one nanosecond, or the amplifying and compressing can be done with a chirped fiber compressor combination, e.g., with the amplified pulses between 1 and 20 nanoseconds in duration.

In one embodiment, repetition rate is used to control pulse energy, the pre-compression optical amplifier's temperature is controlled by, and an active mirror is used in the compressor with the amplification of the active mirror being controlled by current of the active mirror's pump-diodes.

Generally a semiconductor oscillator is used to generate pulses and in some embodiments a SOA preamplifier is used to amplify the selected pulses before introduction into the optically-pumped pulse amplifier. In one embodiment, sub-picosecond pulses of between 10 picoseconds and one nanosecond are used, followed by pulse selection, with the selected pulses amplified by a fiber-amplifier (e.g., a erbium-doped optically-pumped pulse amplifier or EDFA) and compressed by an air-path between gratings compressor (e.g., a Treacy grating compressor), with the compression creating a sub-picosecond ablation pulse.

Compressors could be run with overlapping inputs from more than one amplifier, but reflections from other of the parallel amplifiers can cause a loss of efficiency. With the optically-pumped pulse amplifiers, a nanosecond spacing of sub-nanosecond pulses minimizes amplifying of multiple signals at the same time, and a single compressor is preferably used. High ablative pulse repetition rates are preferred and the total pulses per second (the total system repetition rate) from the one or more parallel optical amplifiers is preferably greater than 0.6 million.

Another alternative is generating a sub-picosecond pulse and time-stretching that pulse within semiconductor pulse generator to give the wavelength-swept-with-time initial pulse for the optically-pumped pulse amplifier. Another alternate is to measure light leakage from the delivery fiber to get a feedback proportional to pulse power and/or energy for control purposes.

Note also that optically-pumped optical pulse amplifiers (including, and those used to pump other optical devices) in general (including, and in such shapes as slabs, discs, and rods) can be controlled. Note further that lamp-pumped can be controlled by controlling the pumping lamps in a manner similar to that of controlling pump diode current. Preferably, active-diode diode pump-current is used to control the amplification of an active mirror. Generally optical pump device (diode or lamp) current is controlled either directly or indirectly by controlling voltage, power, and/or energy. As used herein, controlling current can include shutting off one or more optical pump devices, when multiple pump devices are used.

The present invention provides a method of system operation, wherein the spot is between 10 and 60 microns diameter, and the system is controlled current through an amplifier or pump diodes, and gives a pulse energy density applied to the body is between 2.5 and 3.6 times ablation threshold of the body portion being ablated. Generally it can utilize an optical oscillator in the generation of a series of wavelength-swept-with-time pulses, amplifying the wavelength-swept-with-time pulse with an amplifier, time-compressing the amplified pulse and illuminating the spot on a portion of the body with the time-compressed optical pulse, and scanning the spot over an area. Preferably the pulse repetition rate is at least 0.6 million pulses per second. Preferably the ablation spot size is between 20 and 50 microns in diameter. In some preferred embodiments, the ablation spot size is between 20 and 40 microns in diameter.

Another alternative is generating a sub-picosecond pulse and time-stretching that pulse within semiconductor pulse generator to give the wavelength-swept-with-time initial pulse for the optically-pumped pulse amplifier. For example, the pulse generator can generate pulses at a 50 MHz rate, and the pulses stretched to 20 nanoseconds. The pulse generator need not be shut down during the pause, as the amplifier will only operate while the current is supplied. At 1550 nm compression is much more efficient than at shorter wavelengths, and long stretches can be used, for example operation with a 100 nanosecond stretch or more may be possible.

A beam of high energy, ultra-short (generally sub-picosecond) laser pulses can literally vaporize any material (including steel or even diamond). Such a pulse has an energy-per-unit-area that ionizes the atoms of spot on a surface and the ionized atoms are repelled from the surface. A series of pulses can rapidly create a deep hole. Some machining applications can be done with small (e.g., 10 to 20 micron diameter) spots, but other applications need larger (e.g., 40 to 100 micron) spots. While solid-state laser systems can supply enough energy (in a form compressible to short-enough pulses) for the larger spot sizes, the efficiency of such systems has been very low (generally less than 1%), creating major heat dissipation problems, and thus requiring very expensive systems that provide only slow machining (due to low pulse repetition rates). This system uses a beam pattern within the amplifier and can essentially eliminate heating due to amplified spontaneous emission. The system can operate at a wavelength such that the optical amplifier can be directly pumped by laser diodes emitting wavelengths of greater than 900 nm, further increasing the efficiency. This system can obtain efficiencies of over 30%, lowering the size and cost of the system and greatly increasing machining speed.

The optical pulse amplifiers are more effective operated with the electrical current supplied continuously (only turned off when the ablation is paused or stopped). In the optically pumped amplifier, the input optical signal is a series of wavelength swept with time ramps, (but the ramps are generally not essentially end-to-end), and the repetition rate and/or pump-diode current are controlled to prevent the amplifier from exceeding its maximum stored energy.

In the past, solid-state amplifiers have either been pumped essentially continuously (e.g., for at least many seconds) or pumped on a pulse-by-pulse basis. To operate the system efficiently at high power, the starting and stopping of current from the pump diode power supply should be a small fraction of the number of pulses, and stream of pulses should be limited to sub-millisecond duration (to limit thermal spikes) and pauses are preferably longer than the solid-state material's storage lifetime, but preferably reasonably short (e.g., sub-second, and more preferably sub-millisecond).

The present invention also provides a method of controlling an optical pumped amplifier capable of optical ablation at an ablation rate by directly pumping the amplifier with pump diodes, introducing sub-millisecond streams (bursts) of pulses separated by pauses into amplifier, controlling the ratio of streaming-time to pause-time to control and least one of amplifier-operating-temperature and ablation-rate. The amplifier is operated at a lower than maximum ablation rate, and the ratio of streaming-time to pause-time can be used to vary the ablation rate.

Preferably, the pause is sub-millisecond in duration, the pulses 1 to 20 nanoseconds in duration during amplification (and are later compressed to sub-picosecond in duration), and the amplifier is a solid-state optical amplifier, especially a Cr:YAG amplifier.

In some embodiments, current through the pump diodes is used to control pump diode operating temperature. The repetition rate can be controlled to vary energy of the pulses and preferably the repetition rate of pulses within a stream is at least 220 kHz, and more preferably the repetition rate of pulses within a stream is between 230 kHz and 6 MHz.

Generally the amplifier's optical input signal is a series of light wavelength swept with time pulses (wavelength either increasing or decreasing during the pulse). In the case of the optically pumped amplifier, the input optical signal pulses the ramps are end-to-end), and the repetition rate and/or pump-diode current are controlled to prevent the amplifier from exceeding its maximum stored energy. Thus the pumping power and timing between pulses are controlled such that pumping does not saturate the amplifier material and thus ASE is reduced.

In the past, optically pumped optical amplifiers (e.g., solid-state amplifiers) have generally been pumped by lamps, or occasionally, have been pumped by narrow-band (e.g., 30 nm or less) emitting, thermoelectric-cooled, pump diodes. It has now been found that amplifier systems for such use can be more effective using un-cooled pump diodes where the diodes have a much higher efficiency than lamps, and system efficiency is improved by the elimination of power-cooling devices such as thermoelectric coolers. Preferably, the pump diodes are broadband emission (e.g., bandwidth of 50 nm or more) diodes, such as super-luminescent diodes, and preferably the amplifier is a solid-state amplifier, especially a Cr:YAG amplifier (which also has the advantage of a relatively broad absorption spectrum). The solid-state amplifier can contain a co-dopant, and when the amplifier is a Cr:YAG amplifier, Nd can be used as the co-dopant. In some embodiments, the amplifier contains a co-dopant and the diodes are broadband emission diodes whose emission spectrum overlaps the emission of the co-dopant, and the emission of the diode directs the emission of the co-dopant to more uniformly activate the primary (e.g., Cr) dopant.

Note that the optical amplifier is cooled in many embodiments, including by a heat pipe or by forced air. In some embodiments, a fan is intermittently used to cool the diodes. Note that as used herein, the term "un-controlled-temperature pump diode pumping"means the temperature is not controlled within a narrow temperature range (e.g., within less 5° C.) by a powered "cooler" (such as a thermoelectric cooler which may in some cases be heating, rather than cooling), and not directly or indirectly water-cooled (e.g., not cooled by submersion of the unit in water).

In some high power embodiments, broadband pump diodes are controlled only within a wide range (preferably with only intermittent cooling), such as between −25 and +125° C. The broadband diodes give more uniform penetration of pump light, do not require precise temperature control (they are effective even if their emission spectrum shifts), and they can direct emission from co-dopants.

Ablative material removal previously has been done using systems with optical benches weighing perhaps 1,000 to 2,000 pounds and occupying about 300 cubic feet. The present invention provides a novel system that can weigh less than 100 pounds and occupy less than 2.5 cubic feet. In some embodiments, the man-portable system comprises a cart and/or a backpack, in addition to the probe (and connecting cables). The combination of an efficient amplifier system with a small pulse-compressor enables practical, and significant size reduction, which in turn enables a system in accordance with the present invention to be man-portable, e.g., capable of being moved reasonably easily by one person, such as wheeling a wheeled cart from room to room or even being carried in a backpack.

It has been found that two laser-amplifier/compressor combinations enable practical, and significant size reduction, which in turn enables the system to be man-portable. A used herein, the term "man-portable" means capable of being moved reasonably easily by one person, e.g., as wheeling a wheeled cart from room to room or possibly even being carried in a backpack. In one embodiment, the present invention uses sub-picosecond pulses stretched to between 10 picoseconds and one nanosecond, with the stretched pulse either amplified by a fiber-amplifier (e.g., a erbium-doped fiber amplifier or EDFA) and compressed by an air-path between gratings compressor (e.g., a Treacy grating compressor), with the compression creating a sub-picosecond ablation pulse. Alternately, the present invention uses a semiconductor optical amplifier (SOA) and a with a chirped fiber compressor, generally with pulses stretched to 1 to 20 nanosecond during amplification. Generally, the present invention uses a semiconductor generated initial sub-picosecond pulse in either case and preferably a chirped fiber stretcher in either case (to reduce system size for man-portability), and preferably uses a SOA preamplifier to amplify the initial pulse before introduction into the fiber amplifier.

Previous approaches have generally operated maximum-sized amplifiers at maximum-power and amplifying longer-and-longer pulses. The present invention provides a much smaller and lighter system. A man-portable unit in accordance with the present invention for use in a hospital might include a handheld probe, a vest and control-cart (e.g., a wheeled cart), and receive 120 V power from a wall plug. The handheld probe can contain beam-scanners and optical delivery fibers. The vest can contain optical compressors, and possibly the optical amplifiers (the amplifiers might also be in the cart). The cart can contain the control module, the control panel, the pulse generator, the power supplies, a video camera, a video monitor, air flush system, suction system, and a marker beam generator.

Generally, optical-fiber-containing umbilical cables are used between pieces (e.g., a probe-vest umbilical and a vest-cart umbilical). The umbilical can include a hollow ablation fiber (for pulses compressed to sub-picosecond duration, hollow optical fibers are preferred), a video-camera fiber, an illumination fiber, a marker-beam fiber, an air flush tube, a suction tube and wiring for the scanners.

Alternately, the battery-powered unit could contain a probe, vest, backpack and one or two satchels. The handheld probe could again contain beam-scanners and optical delivery fibers. The vest could contain optical compressors, the optical amplifiers and control devices (e.g., control knobs, switches, etc., that were on the control panel in the cart). The backpack could contain the control module, the pulse generator, the power supplies, a marker beam generator, and a battery pack. A satchel might contain a video camera, a video monitor, an illumination source, and additional batteries. The system might be operable without the satchel, but have additional capabilities including longer operation, with the satchel connected (through a wiring-containing umbilical). In a variation of this alternative, the video camera could be in the backpack and a heads-up display used to provide a video monitor (and a display of control settings) without using a satchel.

The handheld probe preferably contains piezoelectrically-driven-mirror beam-scanners and optical delivery fibers. One delivery fiber has a lens on the fiber-end near the probe tip and can transmit a video image back to the video camera (e.g., in the vest, backpack, satchel or cart). Another fiber can convey illumination to the ablation region. A hollow optical fiber can bring ablation pulses to the beam-scanner mirrors. A fiber can also be used to bring a laser marker beam to the beam-scanner mirrors (where it is scanned in the same manner as the ablation beam). While the laser marker beam can show the entire scan area, it is preferably turned off and on by the specifications of area, color, and distance from target, such that it shows the area that would be ablated if the ablation beam were on (again the marker beam can also change color to indicate whether the ablation beam is on or off). The probe can also contain tubes for suction and/or gas flush.

Initially man-portable units may include several pieces, e.g., a handheld probe, handheld probe, vest/backpack and 2 satchels. Such a unit can be relatively inexpensive and might be used by emergency personnel (e.g., EMTs) in the field. The unit can do emergency cutting of a victim and any needed cauterizing of wounds (it can also be run with longer, e.g., microsecond long, thermally-inducing, pulses to cauterize a wound, either with the same, or a different laser). It can also cut through any obstacles in the way of getting to, or freeing the victim, for example cutting the top of a car loose, or cutting through an I-beam. The size and number of pieces may be reduced later, to a handheld probe, vest, and backpack, for example.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification, but only by the claims.

The invention claimed is:

1. A method of amplifying a polarized input beam, comprising the steps of:
aligning at least four slabs spaced from adjacent slabs, each of the slabs having a thickness dimension of not more than 1 centimeter, wherein slab surfaces of the at least four slabs are placed within about 1 degree of a Brewster angle with respect to the polarized input beam, and no two of the slab surfaces are within 0.1 degree of parallel with respect to each other;
optically pumping the at least four slabs; and
passing the polarized input beam through the slab surfaces, wherein the polarized input beam is optically amplified in the at least four slabs,
wherein half of the slab surfaces are slanted in one direction and half of the slab surfaces are slanted in an opposite direction, the opposite slanting slab surfaces being configured to control spreading of an output beam.

2. The method of claim 1, wherein the at least four slabs comprise Cr:YAG slabs.

3. The method of claim 1, further including passing cooling fluid between the at least four slabs.

4. The method of claim 1, wherein the slab surfaces include dielectric surface coatings.

5. The method of claim 1, further including pumping the at least four slabs using pump diodes.

6. The method of claim 1, wherein the at least four slabs are tilted in a same direction such that a cross-sectional area of a line shaped beam is reduced during amplification.

7. The method of claim 1, wherein the polarized input beam has a wavelength of between 1400 and 1800 nm.

8. The method of claim 1, wherein the thickness dimension is less than 3 millimeters.

9. A method of amplifying an optical beam, comprising the steps of:
aligning at least four optical-amplifier slabs, each of the optical-amplifier slabs having two opposed slab surfaces that are substantially perpendicular to a thickness dimension, the thickness dimension being less than one centimeter, the slab surfaces of a first of the four optical-amplifier slabs being slightly non-parallel to slab surfaces of an adjacent member of the four optical-amplifier slabs, and the first of the four optical-amplifier slabs being separated by an intervening space from the adjacent member of the four optical-amplifier slabs, the slab surfaces being essentially non-reflective;
optically pumping the optical-amplifier slabs; and
passing the optical beam through the slab surfaces to amplify the optical beam, the optical beam being of an eye-safe wavelength,
wherein the optical beam is passed through the at least four optical-amplifier slabs within about 1 degree of a Brewster angle of the slab surfaces, wherein half of the at least four optical-amplifier slabs are slanted in one direction and half of the at least four optical-amplifier slabs are slanted in an opposite direction, the opposite slanting half of the at least four optical-amplifier slabs being configured to control spreading of an output beam.

10. The method of claim 9, wherein the slab surfaces of the first of the four optical-amplifier slabs are not within 0.1 degree of being parallel to each other and are not within 0.1 degree of being parallel to the slab surfaces of other members of the four optical-amplifier slabs.

11. The method of claim 9, wherein the thickness dimension of each optical-amplifier slab is less than 3 mm and a diameter of the slab surfaces is at least 5 mm.

12. The method of claim 9, wherein the optical beam has a wavelength between 1400 and 1800 nm.

13. The method of claim 9, further comprising pumping the at least four optical-amplifier slabs using pump diodes.

14. An amplification system, comprising:
a plurality of wedge-shaped slabs each having a thickness dimension of less than 1 centimeter and two slab surfaces that are slightly non-perpendicular to a thickness dimension, the plurality of wedge-shaped slabs disposed such that facing slab surfaces of adjacent wedge-shaped slabs are slightly non-parallel and the wedge-shaped slabs are separated by an intervening volume;
a cooling fluid in the intervening volume between the adjacent wedge-shaped slabs; and
a polarized input beam passed through the slab surfaces of the wedge-shaped slabs near a Brewster angle,
wherein half of the slab surfaces of the wedge-shaped slabs are slanted in one direction and half of the slab surfaces of the wedge-shaped slabs are slanted in an opposite direction, the opposite slanting slab surfaces of the wedge-shaped slabs being configured to control spreading of an output beam.

15. The amplification system of claim 14, wherein the slab surfaces include an anti-reflection surface coating.

16. The amplification system of claim 14, wherein the polarized input beam has a wavelength of between 1400 nm and 1800 nm.

17. The amplification system of claim 14, wherein the thickness dimension of each wedge-shaped slab is less than 3 mm.

18. An amplification system, comprising:
a plurality of wedge-shaped slabs each having a thickness dimension of less than 1 centimeter and two slab surfaces that are slightly non-perpendicular to a thickness dimension, the plurality of wedge-shaped slabs disposed such that facing slab surfaces of adjacent wedge-shaped slabs are slightly non-parallel and the wedge-shaped slabs are separated by an intervening volume;
a cooling fluid in the intervening volume between the adjacent wedge-shaped slabs; and
a polarized input beam passed through the slab surfaces of the wedge-shaped slabs near a Brewster angle,
wherein one of the slab surfaces of the wedge-shaped slabs includes a grating.

* * * * *